US012570940B2

(12) United States Patent
Daniele et al.

(10) Patent No.: US 12,570,940 B2
(45) Date of Patent: Mar. 10, 2026

(54) TWO-DIMENSIONAL (2D) MODELS OF TISSUE BARRIERS, METHODS OF MAKING AND USING THE SAME

(71) Applicant: North Carolina State University, Raleigh, NC (US)

(72) Inventors: Michael Daniele, Raleigh, NC (US); Ashlyn T. Young, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 1219 days.

(21) Appl. No.: 17/275,263

(22) PCT Filed: Sep. 13, 2019

(86) PCT No.: PCT/US2019/051103
§ 371 (c)(1),
(2) Date: Mar. 11, 2021

(87) PCT Pub. No.: WO2020/056320
PCT Pub. Date: Mar. 19, 2020

(65) Prior Publication Data
US 2021/0324316 A1 Oct. 21, 2021

Related U.S. Application Data

(60) Provisional application No. 62/730,737, filed on Sep. 13, 2018.

(51) Int. Cl.
*C12M 3/00* (2006.01)
*B01L 3/00* (2006.01)
(Continued)

(52) U.S. Cl.
CPC ............ *C12M 23/16* (2013.01); *C12M 21/08* (2013.01); *C12M 25/14* (2013.01)

(58) Field of Classification Search
CPC ....... C12M 25/14; C12M 21/08; C12M 23/16
See application file for complete search history.

(56) References Cited

U.S. PATENT DOCUMENTS 9,157,060 B2 10/2015 Ligler et al.
9,926,534 B2 3/2018 Adams et al.
(Continued)

FOREIGN PATENT DOCUMENTS

WO 2006/052223 A1 5/2006

OTHER PUBLICATIONS

Abaci et al., "Human-on-a-chip design strategies and principles for physiologically based pharmacokinetics/pharmacodynamics modeling," Integrative Biology, Apr. 2015, vol. 7, Issue 4, pp. 383-391.
(Continued)

*Primary Examiner* — Nathan A Bowers
(74) *Attorney, Agent, or Firm* — Thomas|Horstemeyer, LLP

(57) ABSTRACT

Described herein are two-dimensional (2D) models of tissue barriers, methods of making and using the same, and on-model analysis techniques. Aspects of the present disclosure include systems and methods relating to microfluidic tissue models, in particular those of the vasculature-endothelial barrier. Systems and methods as described herein can utilize impedance mapping to assess model conditions in response to stimuli, for example the introduction of pharmaceutical compositions.

20 Claims, 32 Drawing Sheets

(51) Int. Cl.
C12M 1/12 (2006.01)
C12M 3/06 (2006.01)

(56) References Cited

U.S. PATENT DOCUMENTS

| | | | |
|---|---|---|---|
| 2006/0019361 A1 | 1/2006 | Ng et al. | |
| 2008/0233607 A1* | 9/2008 | Yu | C12M 23/34 |
| | | | 435/299.1 |
| 2010/0204065 A1 | 8/2010 | Kim et al. | |
| 2011/0159522 A1* | 6/2011 | Kamm | G01N 33/5029 |
| | | | 435/287.1 |
| 2013/0288292 A1* | 10/2013 | Meyvantsson | B01L 3/502746 |
| | | | 435/309.1 |
| 2014/0057311 A1* | 2/2014 | Kamm | G01N 33/5029 |
| | | | 216/33 |
| 2014/0212910 A1* | 7/2014 | Bhatia | C12Q 1/02 |
| | | | 425/5 |
| 2015/0301027 A1 | 10/2015 | Charest et al. | |
| 2016/0130543 A1 | 5/2016 | Daniele et al. | |
| 2018/0064527 A1 | 3/2018 | Adams et al. | |
| 2018/0085750 A1* | 3/2018 | Varghese | B01L 3/502707 |
| 2018/0172666 A1* | 6/2018 | Chung | C12M 25/14 |

OTHER PUBLICATIONS

Allen et al., "Formation of Steady-State Oxygen Gradients In Vitro: Application to Liver Zonation," Biotechnology and Bioengineering, May 2003, vol. 82, No. 3, pp. 253-262.

Allen et al., "In Vitro Zonation and Toxicity in a Hepatocyte Bioreactor," Toxicological Sciences, Mar. 2005, vol. 84, No. 1, pp. 110-119.

Arnold et al., "In-Situ Near Infrared Spectroscopy to Monitor Key Analytes in Mammalian Cell Cultivation," Biotechnology and Bioengineering, Oct. 2003, vol. 84, No. 1, pp. 13-19.

Bagnaninchi et al., "Real-time label-free monitoring of adipose-derived stem cell differentiation with electric cell-substrate impedance sensing, " PNAS, Apr. 2011, vol. 108, No. 16, pp. 6462-6467.

Banaeiyan et al., "Design and fabrication of a scalable liver-lobule-on-a-chip microphysiological platform," Biofabrication, Feb. 2017, vol. 9, No. 015014.

Bavli et al., "Real-time monitoring of metabolic function in liver-on-chip microdevices tracks the dynamics of mitochondrial dysfunction," PNAS, Apr. 2016, vol. 113, No. 16, E2231-E3340.

Benson et al., "Impedance-based cell monitoring: barrier properties and beyond," Fluids and Barriers of the CNS, Jan. 2013, vol. 10, No. 5.

Beutel et al., "In situ sensor techniques in modern bioprocess monitoring," Applied Microbiology and Biotechnology, Jul. 2011, vol. 91, pp. 1493-1505.

Biechele et al., "Sensor systems for bioprocess monitoring," Engineering in Life Sciences, Apr. 2015, vol. 15, No. 5, pp. 469-488.

Biselli et al., "Organs on chip approach: a tool to evaluate cancer-immune cells interactions," Scientific Reports, Oct. 2017, vol. 7, No. 12737.

Bluma et al., "In-situ imaging sensors for bioprocess monitoring: state of the art," Analytical and Bioanalytical Chemistry, Sep. 2010, vol. 398, pp. 2429-2438.

Bonk et al., "Design and Characterization of a Sensorized Microfluidic Cell-Culture System with Electro-Thermal Micro-Pumps and Sensors for Cell Adhesion, Oxygen, and pH on a Glass Chip," Biosensors, Jul. 2015, vol. 5, pp. 513-536.

Boudou et al., "A Microfabricated Platform to Measure and Manipulate the Mechanics of Engineered Cardiac Microtissues," Tissue Engineering: Part A, May 2012, vol. 18, Nos. 9-10, pp. 910-919.

Caballero et al., "Organ-on-chip models of cancer metastasis for future personalized medicine: From chip to the patient," Biomaterials, Dec. 2017, vol. 149, pp. 98-115.

Canali et al., "Bioimpedance monitoring of 3D cell culturing—Complementary electrode configurations for enhanced spatial sensitivity," Biosensors and Bioelectronics, Jan. 2015, vol. 63, pp. 72-79.

Cho et al., "Organ-on-a-chip for assessing environmental toxicants," Current Opinion in Biotechnology, Jun. 2017, vol. 45, pp. 34-42.

Clark et al., "Continuous-Flow Enzyme Assay on a Microfluidic Chip for Monitoring Glycerol Secretion from Cultured Adipocytes," Analytical Chemistry, Mar. 2009, vol. 81, No. 6, pp. 2350-2356.

Dash et al., "Liver tissue engineering in the evaluation of drug safety," Expert Opinion on Drug Metabolism & Toxicology, Oct. 2009, vol. 5, No. 10, pp. 1159-1174.

Domansky et al., "Perfused multiwell plate for 3D liver tissue engineering," Lab Chip, Jan. 2010, vol. 10, pp. 51-58.

Domenech et al., "Cellular observations enabled by microculture: paracrine signaling and population demographics," Integrative Biology, Mar. 2009, vol. 1, Issue 3, pp. 267-274.

Doryab et al., "Advances in pulmonary therapy and drug development: Lung tissue engineering to lung-on-a-chip," Biotechnology Advances, Feb. 2016, vol. 34, pp. 588-596.

Du et al., "Mimicking liver sinusoidal structures and functions using a 3D-configured microfluidic chip," Lab Chip, Mar. 2017, vol. 17, No. 5, pp. 741-964.

Faley et al., "Microfluidic single cell arrays to interrogate signalling dynamics of individual patient-derived hematopoietic stem cells," Lab Chip, Sep. 2009, vol. 9, pp. 2659-2664.

Ge et al., "Validation of an optical sensor-based high-throughput bioreactor system for mammalian cell culture," Journal of Biotechnology, Apr. 2006, vol. 122, pp. 293-306.

Geraili et al., "Controlling Differentiation of Stem Cells for Developing Personalized Organ-on-Chip Platforms," Advanced Healthcare Materials, Jan. 2018, vol. 7, No. 1700426.

Ghenim et al., "Monitoring impedance changes associated with motility and mitosis of a single cell," Lab Chip, Aug. 2010, vol. 10, pp. 2546-2550.

Giaever et al., "Monitoring fibroblast behavior in tissue culture with an applied electric field," PNAS, Jun. 1984, vol. 31, pp. 3761-3764.

Henry et al., "Organ-on-chips with integrated electrodes for transepithelial electrical resistance TEER measurements of human epithelial barrier function," Lab Chip, Jun. 2017, vol. 17, No. 13, pp. 2264-2271.

Hong et al., "Electrical cell-substrate impedance sensing as a non-invasive tool for cancer cell study," Analyst, Jan. 2011, vol. 136, pp. 237-245.

Hu et al., "A novel microphysiometer based on high sensitivity LAPS and microfluidic system for cellular metabolism study and rapid drug screening," Biosensors and Bioelectronics, Feb. 2013, vol. 40, pp. 167-173.

Joeris et al., "In-situ microscopy: Online process monitoring of mammalian cell cultures," Cytotechnology, 2002, vol. 38, pp. 129-134.

Kalman et al., "Engineering human 3D micromuscles with co-culture of fibroblasts and myoblasts," Computer Methods in Biomechanics and Biomedical Engineering, Aug. 2015, vol. 18, pp. 1960-1961.

Khazali et al., "A Pathway to Personalizing Therapy for Metastases Using Liver-on-a-Chip Platforms," Stem Cell Reviews and Reports, Apr. 2017, vol. 13, No. 3, pp. 364-380.

Khazali et al., "Inflammatory cytokine IL-8/CXCL8 promotes tumour escape from hepatocyte-induced dormancy," British Journal of Cancer, Feb. 2018, vol. 118, pp. 566-576.

Kilic et al., "Organs-on-chip monitoring: sensors and other strategies," Microphysiological Systems, Sep. 2018, vol. 2, No. 5.

Kim et al., "A mini-microscope for in situ monitoring of cells," Lab Chip, Oct. 2012, vol. 12, pp. 3976-3982.

Kim et al., "A quantitative microfluidic angiogenesis screen for studying anti-angiogenic therapeutic drugs," Lab Chip, Jan. 2015, vol. 15, pp. 301-310.

Kim et al., "Vasculature-On-A-Chip for In Vitro Disease Models," Bioengineering, Jan. 2017, vol. 4, No. 8.

Kodzius et al., "Organ-on-Chip Technology: Current State and Future Developments," Genes, Oct. 2017, vol. 8, No. 266.

Lafleur et al., "A rapid, instrument-free, sample-to-result nucleic acid amplification test," Lab Chip, Sep. 2016, vol. 16, pp. 3777-3787.

(56)        References Cited

OTHER PUBLICATIONS

Lanz et al., "Therapy response testing of breast cancer in a 3D high-throughput perfused microfluidic platform," BMC Cancer, Nov. 2017, vol. 17, No. 709.
Le et al., "Cell line development for biomanufacturing processes: recent advances and an outlook," Biotechnology etters, May 2015, vol. 37, pp. 1553-1564.
Lee et al., "An Artificial Liver Sinusoid With a Microfluidic Endothelial-Like Barrier for Primary Hepatocyte Culture," Biotechnology and Bioengineering, Aug. 2007, vol. 97, No. 5, pp. 1340-1346.
Lee, L. P., "Microphysiological Analytic Platforms MAPs: Precision Organs on Chip," Advanced Healthcare Materials, 2018, vol. 7, No. 1701488.
Lei et al., "Real-time and non-invasive impedimetric monitoring of cell proliferation and chemosensitivity in a perfusion BD cell culture microfluidic chip," Biosensors and Bioelectronics, Jan. 2014, vol. 51, pp. 16-21.
Lei et al., "Towards a high throughput impedimetric screening of chemosensitivity of cancer cells suspended in hydrogel and cultured in a paper substrate," Biosensors and Bioelectronics, Feb. 2018, vol. 100, pp. 355-360.
Lewis et al., "The Use of 'Omics Technology to Rationally Improve Industrial Mammalian Cell Line Performance," Biotechnology and Bioengineering, Jan. 2016, vol. 113, No. 1, pp. 26-38.
Lind et al., "Instrumented cardiac microphysiological devices via multimaterial three-dimensional printing," Nature Materials, Mar. 2017, vol. 16, pp. 303-308.
Liu et al., "Impedance studies of bio-behavior and chemosensitivity of cancer cells by micro-electrode arrays," Biosensors and Bioelectronics, Jan. 2009, vol. 24, pp. 1305-1310.
Extended European Search Report for related application No. 19858740.4-1111 dated May 12, 2022.
Toh Y-C et al: "A configurable three-dimensional microenvironment in a microfluidic channel for primary hepatocyte culture", Assay and Drug Development Technologies,, vol. 3, No. 2, Jan. 1, 2005 (Jan. 1, 2005), pp. 169-176, XP008116416, DOI: 10.1089/ADT.2005.3.169.
International Search Report and Written Opinion for PCT/US2019/051103 mailed on Jan. 17, 2020.
Van der Helm, M, et al. "Microfluidic organ-on-chip technology for blood-brain barrier research." Tissue barriers vol. 4.1 (2018): e1142493.
Srinivasan, B, et al. "TEER measurement techniques for in vitro barrier model systems." J Lab Autom 20.2 (2015): 107-26.
Young, A, et al. "Monitoring of Microphysiological Systems: Integrating Sensors and Real-Time Data Analysis toward Autonomous Decision-Making" ACS Sens. 4.6 (2019): 1454-1464.
Liu et al., "Microdevice arrays with strain sensors for 3D mechanical stimulation and monitoring of engineered tissues," Biomaterials, Jul. 2018, vol. 172, pp. 30-40.
Maoz et al., "A linked organ-on-chip model of the human neurovascular unit reveals the metabolic coupling of endothelial and neuronal cells," Nature Biotechnology, Sep. 2018, vol. 36, No. 9, pp. 865-874.
Marx et al., "Biology-inspired Microphysiological System Approaches to Solve the Prediction Dilemma of Substance Testing," ALTEX, Aug. 2016, vol. 33, No. 3, pp. 272-321.
Matsuoka et al., "Morphology-Based Prediction of Osteogenic Differentiation Potential of Human Mesenchymal Stem Cells," PLoS One, Feb. 2013, vol. 8, No. 2, e55082.
Mehta et al., "Quantitative measurement and control of oxygen levels in microfluidic polydimethylsiloxane bioreactors during cell culture," Biomedical Microdevices, Apr. 2007, vol. 9, pp. 123-134.
Mirasoli et al., "Recent advancements in chemical luminescence-based lab-on-chip and microfluidic platforms for bioanalysis," Journal of Pharmaceutical and Biomedical Analysis, Jan. 2014, vol. 87, pp. 36-52.
Misun et al., "Multi-analyte biosensor interface for real-time monitoring of 3D microtissue spheroids in hanging-drop hetworks," Microsystems & Nanoengineering, Jun. 2016, vol. 2, No. 16022.

Modena et al., "Smart Cell Culture Systems: Integration of Sensors and Actuators into Microphysiological Systems," ACS Chemical Biology, Jan. 2018, vol. 13, No. 7, pp. 1767-1784.
Nguyen et al., "Microfluidic Chip with Integrated Electrical Cell-Impedance Sensing for Monitoring Single Cancer Cell Migration in Three-Dimensional Matrixes," Analytical Chemistry, Oct. 2013, vol. 85, No. 22, pp. 11068-11076.
Nguyen et al., "Versatile synthetic alternatives to Matrigel for vascular toxicity screening and stem cell expansion," Nature Biomedical Engineering, Jul. 2017, vol. 1, No. 0096.
Oyunbaatar et al., "Biomechanical Characterization of Cardiomyocyte Using PDMS Pillar with Microgrooves," Sensors, Aug. 2016, vol. 16, No. 1258.
Pemberton et al., "Fabrication and Evaluation of a MicroBioSensor Array Chip for Multiple Parallel Measurements of Important Cell Biomarkers," Sensors, Nov. 2014, vol. 14, pp. 20519-20532.
Pereira Rodrigues et al., "Cell-based microfluidic biochip for the electrochemical real-time monitoring of glucose and oxygen," Sensors and Actuators B: Chemical, Jun. 2008, vol. 132, Issue 2, pp. 608-613.
Prantil-Baun et al., "Physiologically Based Pharmacokinetic and Pharmacodynamic Analysis Enabled by Microfluidically Linked Organs-on-Chips," Annual Review of Pharmacology and Toxicology, 2018, vol. 58, pp. 37-64.
Prill et al., "Long-term microfluidic glucose and lactate monitoring in hepatic cell culture," Biomicrofluidics, May 2014, vol. 8, No. 034102.
Prill et al., "Real-time monitoring of oxygen uptake in hepatic bioreactor shows CYP450-independent mitochondrial toxicity of acetaminophen and amiodarone," Archives of Toxicology, 2016, vol. 90, pp. 1181-1191.
Riahi et al., "Automated microfluidic platform of bead-based electrochemical immunosensor integrated with bioreactor for continual monitoring of cell secreted biomarkers," Scientific Reports, Apr. 2016, vol. 6, No. 24598.
Riordon et al., "Deep Learning with Microfluidics for Biotechnology," Trends in Biotechnology, Mar. 2019, vol. 37, Issue 3, pp. 310-324.
Rivera et al., "Integrated phosphorescence-based photonic biosensor iPOB for monitoring oxygen levels in 3D cell culture systems," Biosensors and Bioelectronics, Jan. 2019, vol. 123, pp. 131-140.
Sandor et al., "Comparative study of non-invasive monitoring via infrared spectroscopy for mammalian cell cultivations," Journal of Biotechnology, Dec. 2013, vol. 168, pp. 636-645.
Scheper et al., "Bioanalytics: detailed insight into bioprocesses," Analytica Chimica Acta, Apr. 1999, vol. 400, Issues 1-3, pp. 121-134.
Shin et al., "Aptamer-Based Microfluidic Electrochemical Biosensor for Monitoring Cell-Secreted Trace Cardiac Biomarkers," Analytical Chemistry, Sep. 2016, vol. 88, pp. 10019-10027.
Shin et al., "Label-Free and Regenerative Electrochemical Microfluidic Biosensors for Continual Monitoring of Cell Secretomes," Advanced Science, Mar. 2017, vol. 4, No. 1600522.
Simmons et al., "Sensing metabolites for the monitoring of tissue engineered construct cellularity in perfusion bioreactors," Biosensors and Bioelectronics, Apr. 2017, vol. 90, pp. 443-449.
Skardal et al., "Multi-tissue interactions in an integrated three-tissue organ-on-a-chip platform," Scientific Reports, Aug. 2017, vol. 7, No. 8837.
Son et al., "Detecting cell-secreted growth factors in microfluidic devices using bead-based biosensors," Microsystems & Nanoengineering, Jul. 2017, vol. 3, No. 17025.
Stoll et al., "A simple HPLC technique for accurate monitoring of mammalian cell metabolism," Cytotechnology, 1994, vol. 14, pp. 123-128.
Takebe et al., "Synergistic Engineering: Organoids Meet Organs-on-a-Chip," Cell Stem Cell, Sep. 2017, vol. 21, No. 3, pp. 297-300.
Takehara et al., "On-chip cell analysis platform: Implementation of contact fluorescence microscopy in microfluidic chips," AIP Advances, 2017, vol. 7, No. 095213.
Tilles et al., "Effects of Oxygenation and Flow on the Viability and Function of a Rat Hepatocytes Cocultured in a Microchannel

(56)      References Cited

OTHER PUBLICATIONS

Flat-Plate Bioreactor," Biotechnology and Bioengineering, Jun. 2001, vol. 73, No. 5, pp. 379-389.

Timez et al., "Sub-nanoliter, real-time flow monitoring in microfluidic chips using a portable device and smartphone," Scientific Reports, Jul. 2018, vol. 8, No. 10603.

Tsamandouras et al., "Quantitative Assessment of Population Variability in Hepatic Drug Metabolism Using a Perfused Three-Dimensional Human Liver Microphysiological System," Journal of Pharmacology and Experimental Therapeutics, Jan. 2017, vol. 360, No. 1, pp. 95-105.

Urban et al., "Deep Learning for Drug Discovery and Cancer Research: Automated Analysis of Vascularization Images," IEEE/ACM Transactions on Computational Biology and Bioinformatics, May/Jun. 2019, vol. 16, No. 3, pp. 1029-1035.

Wang et al., "Microfluidic Blood-Brain Barrier Model Provides In Vivo-Like Barrier Properties for Drug Permeability Screening," Biotechnology and Bioengineering, Jan. 2017, vol. 114, No. 1, pp. 184-194.

Ware et al., "Engineered Liver Platforms for Different Phases of Drug Development," Trends in Biotechnology, Feb. 2017, vol. 35, No. 2, pp. 172-183.

Weltin et al., "Accessing 3D microtissue metabolism: Lactate and oxygen monitoring in hepatocyte spheroids," Biosensors and Bioelectronics, Jan. 2017, vol. 87, pp. 941-948.

Wikswo, J. P., "The relevance and potential roles of microphysiological systems in biology and medicine," Experimental Biology and Medicine, Sep. 2014, vol. 239, No. 9, pp. 1061-1072.

Xiao et al., "A microfluidic culture model of the human reproductive tract and 28-day menstrual cycle," Nature Communications, Mar. 2017, vol. 8, No. 14584.

Xiao et al., "New physiologically-relevant liver tissue model based on hierarchically cocultured primary rat hepatocytes with liver endothelial cells," Integrative Biology, Nov. 2017, vol. 7, pp. 1412-1422.

Zhang et al., "A cost-effective fluorescence mini-microscope for biomedical applications," Lab Chip, Aug. 2015, vol. 15, pp. 3661-3669.

Zhang et al., "High-Throughput Assessment of Drug Cardiac Safety Using a High-Speed Impedance Detection Technology-Based Heart-on-a-Chip," Micromachines Basel, Jul. 2016, vol. 7, No. 122.

Zhang et al., "Multifunctional 3D electrode platform for real-time in situ monitoring and stimulation of cardiac tissues," Biosensors and Bioelectronics, Jul. 2018, vol. 112, pp. 149-155.

Zhang et al., "Organ-on-a-chip devices advance to market," Lab Chip, Jul. 2017, vol. 17, No. 14, pp. 2395-2420.

Zhang et al., "Multisensor-integrated organs-on-chips platform for automated and continual in situ monitoring of organoid behaviors," PNAS, Mar. 2017, vol. 114, No. 12, E2293-E2302.

Zheng et al., "Organ-on-a-Chip Systems: Microengineering to Biomimic Living Systems," Small, Feb. 2016, vol. 12, No. 17, pp. 2253-2282.

Zhou et al., "Liver injury-on-a-chip: microfluidic co-cultures with integrated biosensors for monitoring liver cell signaling during injury," Lab Chip, Oct. 2015, vol. 15, pp. 4467-4479.

Zhou et al., Mammalian Cell Cultures for Biologics Manufacturing, Advances in Biochemical Engineering/Biotechnology, Springer, Berlin, Heidelberg, vol. 139, 2016.

Zydney, A. L., "Perspectives on integrated continuous bioprocessing—opportunities and challenges," Current Opinion in Chemical Engineering, Nov. 2015, vol. 10, pp. 9-13.

* cited by examiner endothelial cells adhere to scaffold wall no flow, device placed on side (4)

endothelial cells suspended in media flow direction (3)

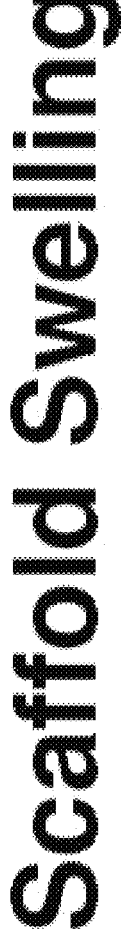
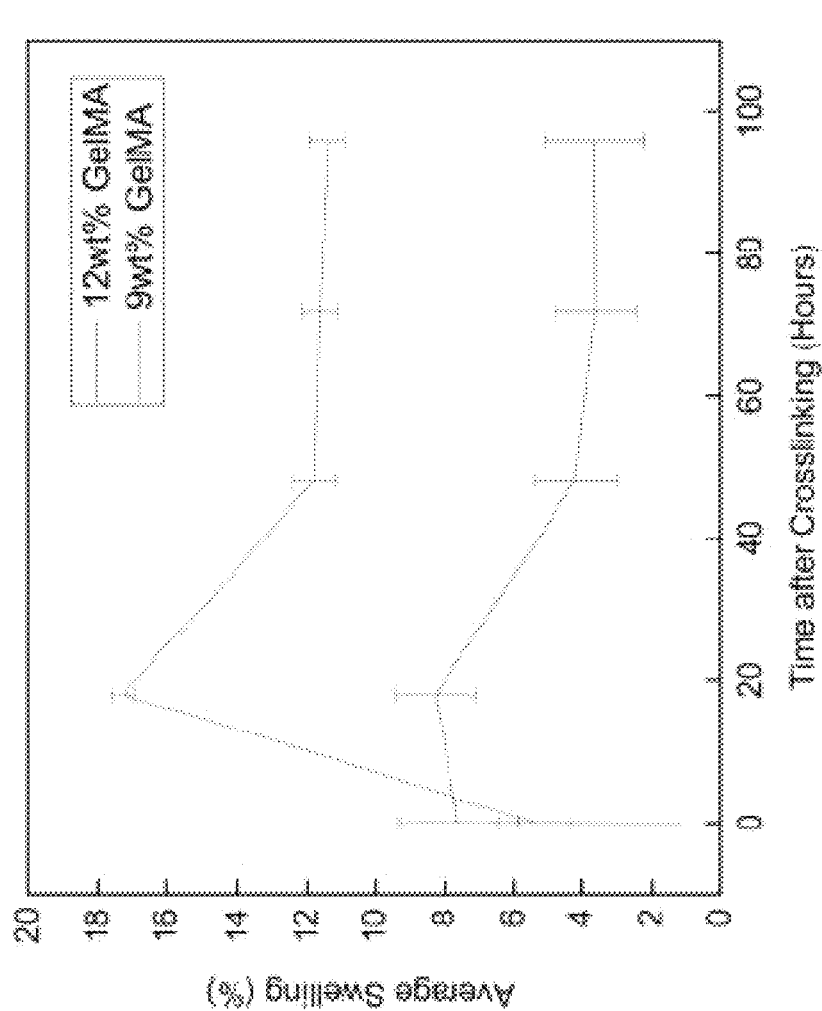
FIG. 11B

Flow rate
Comparison

1:1

3:2

2:1

FIG. 20D
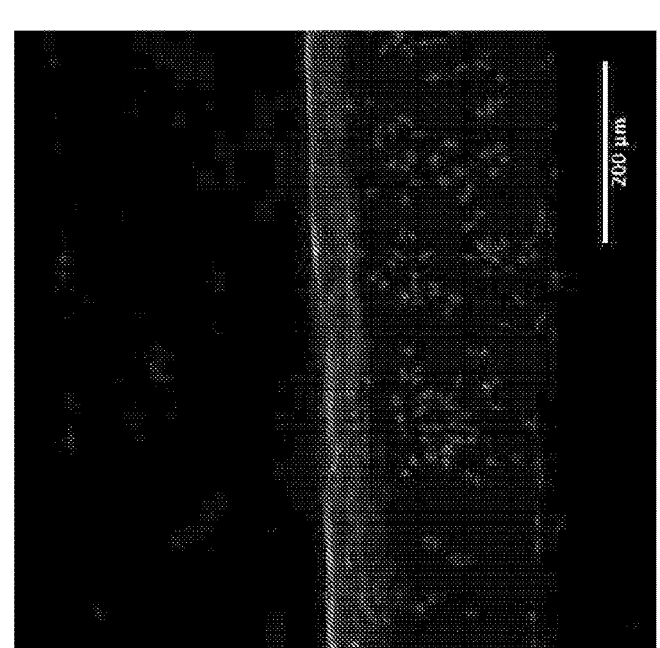
FIG. 20C
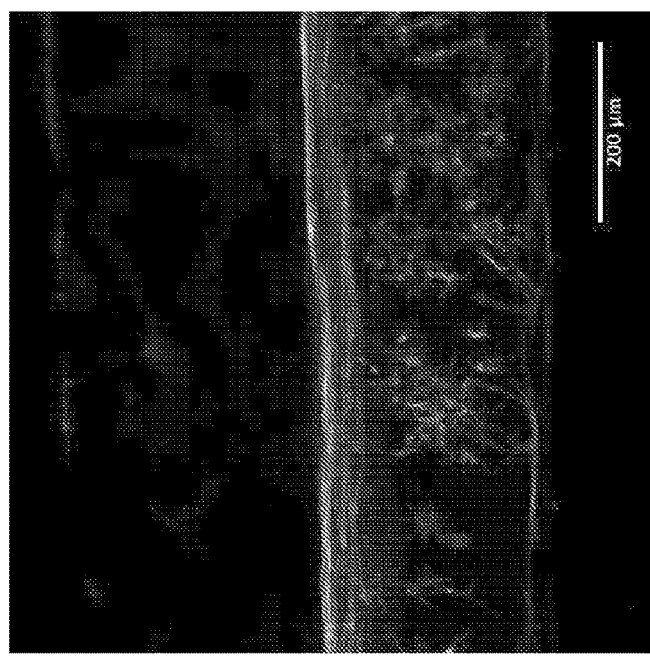
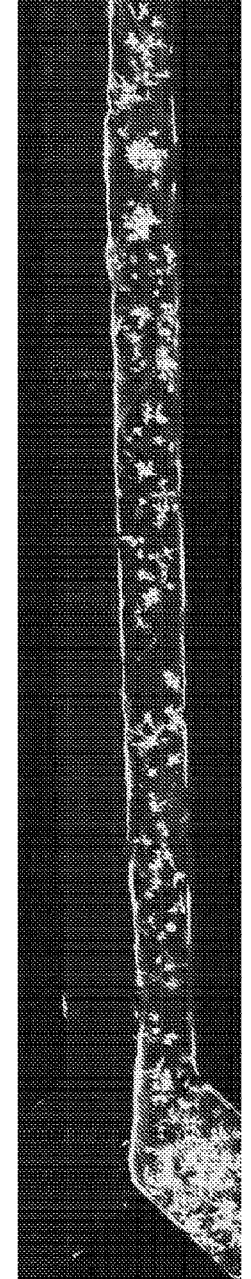
FIG. 20E

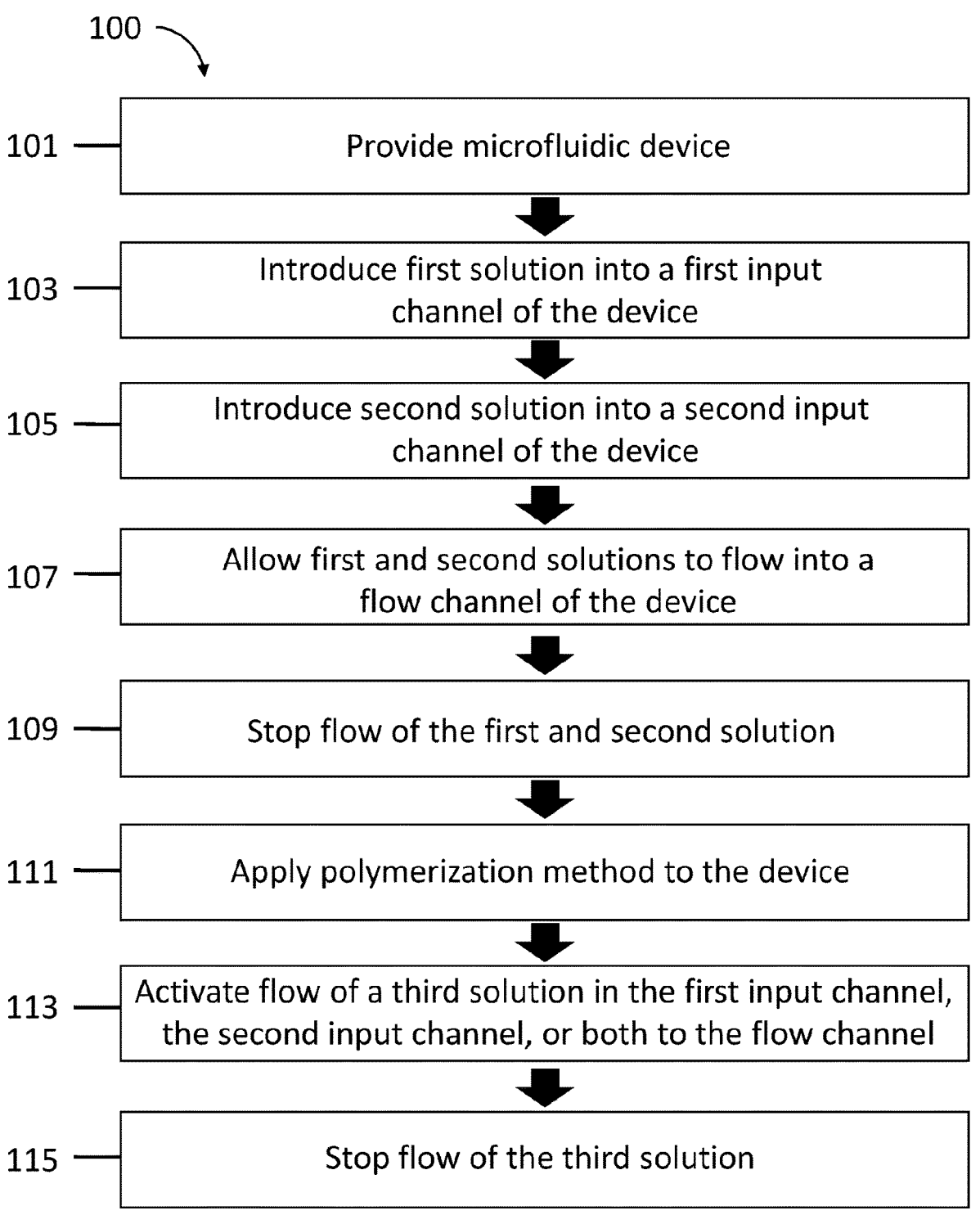

100

101 — Provide microfluidic device

103 — Introduce first solution into a first input channel of the device

105 — Introduce second solution into a second input channel of the device

107 — Allow first and second solutions to flow into a flow channel of the device 109 — Stop flow of the first and second solution 111 — Apply polymerization method to the device 113 — Activate flow of a third solution in the first input channel, the second input channel, or both to the flow channel 115 — Stop flow of the third solution

TWO-DIMENSIONAL (2D) MODELS OF TISSUE BARRIERS, METHODS OF MAKING AND USING THE SAME

CROSS-REFERENCE TO RELATED APPLICATION

This application is the 35 U.S.C. § 371 national stage application of PCT Application No. PCT/US2019/051103, filed Sep. 13, 2019, where the PCT claims priority to and benefit of U.S. Provisional Application 62/730,737 titled "TWO-DIMENSIONAL (2D) MODELS OF TISSUE BARRIERS, METHODS OF MAKING AND USING THE SAME" filed Sep. 13, 2018, the entire disclosures of which are incorporated herein by reference.

TECHNICAL FIELD

The present disclosure generally relates to two-dimensional (2D) models of tissue barriers, methods of making and using the same, and on-model analysis techniques.

BACKGROUND

Existing systems and devices aimed at modeling tissue barriers utilize plastic membranes to separate types of cells in culture. The use of a barrier material can preclude the use of a truely physiologically relevant and viable system. For example, semi-permeable membranes (such as plastic membranes) can block the tissue interface, and prevent the interaction of cells and other elements introduced into the systems, for example antagonists or agonists (small molecules, peptides, nucleic acids, etc). Accordingly, there is a need to address the aforementioned deficiencies and inadequacies and a need for more physiologically-relevant model systems.

SUMMARY

In aspects of the present disclosure, described herein are methods of making tissue models, methods of using tissue models, tissue models, and the like.

In aspects according to the present disclosure, disclosed herein are methods of making tissue models. In an embodiment, a method of making a tissue model comprises making a model with stop-flow polymerization. In an embodiment, a method of making a tissue model, comprises providing a microfluidic device, wherein the microfluidic device comprises two or more input channels on a first end of the device, the two or more input channels converging into a single flow channel in the middle of the device and forming a singular output channel on a second end of the device; providing a first solution into a first channel of the two or more input channels; providing a second solution into a second channel of the two or more input channels, the second solution comprising a scaffold material; allowing the first and the second solution to flow into the flow channel through laminar flow; stopping flow of the first and second solution; polymerizing the scaffold with a polymerization method; activating flow of a third solution in the first channel, second channel, or both; and stopping the flow of the third solution.

The first solution can comprise a cell-adherent coating, a scaffold, or both. The second solution can comprise a scaffold. The cell-adherent coating can be gelatin. The scaffold material of the second solution can be a hydrogel. The scaffold material of the second solution can be polymerized with light (for example UV). The second solution can comprise a hydrogel (i.e. scaffold material) and a first cell type. The first cell type can be a fibroblast. The first cell type can be an endothelial cell. The first cell type can be a vascular endothelial cell. In an embodiment, the hydrogel is gelatin methacryloyl. The first solution or the second solution can further comprise one or more cells. The first solution or the second solution can further comprise one or more cell types. A polymerization method according to the present disclosure can be applying UV light from a UV light source. The third solution can comprise a second cell type and a cell media (for example a cell growth media). The second cell type can be an endothelial cell. The microfluidic device can further comprise a plurality of electrode pairs in electrical connection with the flow channel. The flow rate of the first solution to first solution can be about 1:1 to about 1:100. The flow rate of the first solution to first solution can be about 100:1 to about 1:1.

Described herein are tissue models created by methods as described herein.

Described herein are methods of using a tissue model. In an embodiment, a method of using a tissue model as described herein comprises providing a tissue model; providing a solution comprising a pharmaceutical composition into the first channel of the tissue model, second channel, or both; allowing the solution to flow through the flow channel; mapping the electrical impedance of the flow channel with the plurality of electrode pairs before, during, or after the flow, individually or in combination. In an embodiment, mapping the electrical impedance is performed without a reference electrode. A pharmaceutical composition can comprise a small molecule, peptide, or nucleic acid, individually or in combination. Methods as described herein can further comprise placing the microfluidic device on a longest side with the smallest height.

Described herein are tissue models. A tissue model can comprise a first microfluidic input channel; a second microfluidic input channel; and a microfluidic flow channel. The microfluidic flow channel can be in fluidic communication with the first microfluidic input channel and second microfluidic input channel, and an end of the microfluidic flow channel is configured to receive flow from the first microfluidic input channel and second microfluidic input channel. In an embodiment, a tissue model can be configured so that flow from the first microfluidic input channel and second microfluidic input channel converges at the end of the microfluidic flow channel that receives the flow from the first and second microfluidic flow channels. A tissue model can further comprise a microfluidic output channel in fluidic communication with the microfluidic flow channel, wherein the microfluidic output channel is configured to receive flow from the microfluidic flow channel. One or more inner surfaces of the microfluidic flow channel of the tissue model can comprise a polymeric scaffold. The polymeric scaffold can comprise a photopolymerizable material. The polymeric scaffold further can further comprise a first plurality of cells. The first plurality of cells can be endothelial cells. The first plurality of cells can be fibroblasts or vascular endothelial cells, individually or in combination. Tissue models can further comprise a second plurality of cells seeded on the first plurality of cells. The second plurality of cells can comprise neurons or glia, individually or in combination. The glia can be one or more astrocytes, migroglia, or pericytes. In an embodiment, the second plurality of cells comprises neurons and astrocytes.

Tissue models as described herein can further comprise a plurality of electrode pairs embedded in the flow channel configured to monitor impedence across the length of the channel. The tissue model can comprise 6 to 180 electrodes (3 to 90 electrode pairs). In embodiments, the tissue model does not comprise a reference electrode. In embodiments, the tissue model does not comprise a synthetic (i.e. non-living) semi-permeable membrane. Tissue models as described herein can comprise a potentiostat. In an embodiment, the tissue model comprises 60 electrodes. In embodiments, the polymeric scaffold of tissue models as described herein comprises gelatin methacryloyl, methacrylated collagen, or PEG-derivatives, individually or in combination. The polymeric scaffold can further comprise gelatin or PEG, individually or in combination. The polymeric scaffold can further comprise a photoinitiator.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 11A-11B are maps and data showing scaffold swelling and thickness over time, and illustrating that laminar flow can control shape.

FIG. 14A shows a 60 electrode array that can be used for impedance monitoring of mapping of the flow channel. FIG. 14B is an enlarged view showing an embodiment of additional aspects of the tissue model.

FIGS. 20A-20E: FIGS. 20A-20B BBB-MPS illustrate microfluidic tissue fabrication. Human dermal fibroblasts are embedded in the scaffold, endothelial cells adhere to the tissue wall. FIGS. 20C-20E show immunofluorescent analysis of complete tissue and vessel structure in device. Phalloidin-stained actin (green) fibroblasts and hBMVECs, CD31(red) hBMVECs, and DAPI (blue) nuclei.

FIGS. 21A and 21B are photographs of a 60-electrode array (FIG. 21A), along the channel length of which is used to collect two-point impedance measurements via a multiplexer, potentiostat, and custom Labview code (FIG. 21B). FIG. 21C is an enlarged view showing impedance mapping of insulating glass beads within polymerized scaffold.

FIG. 22 is a flowchart representative of an embodiment of a method of making a tissue barrier as described herein.

FIG. 25B is an enlarged view thereof.

DETAILED DESCRIPTION

Figures 1A, 1B:
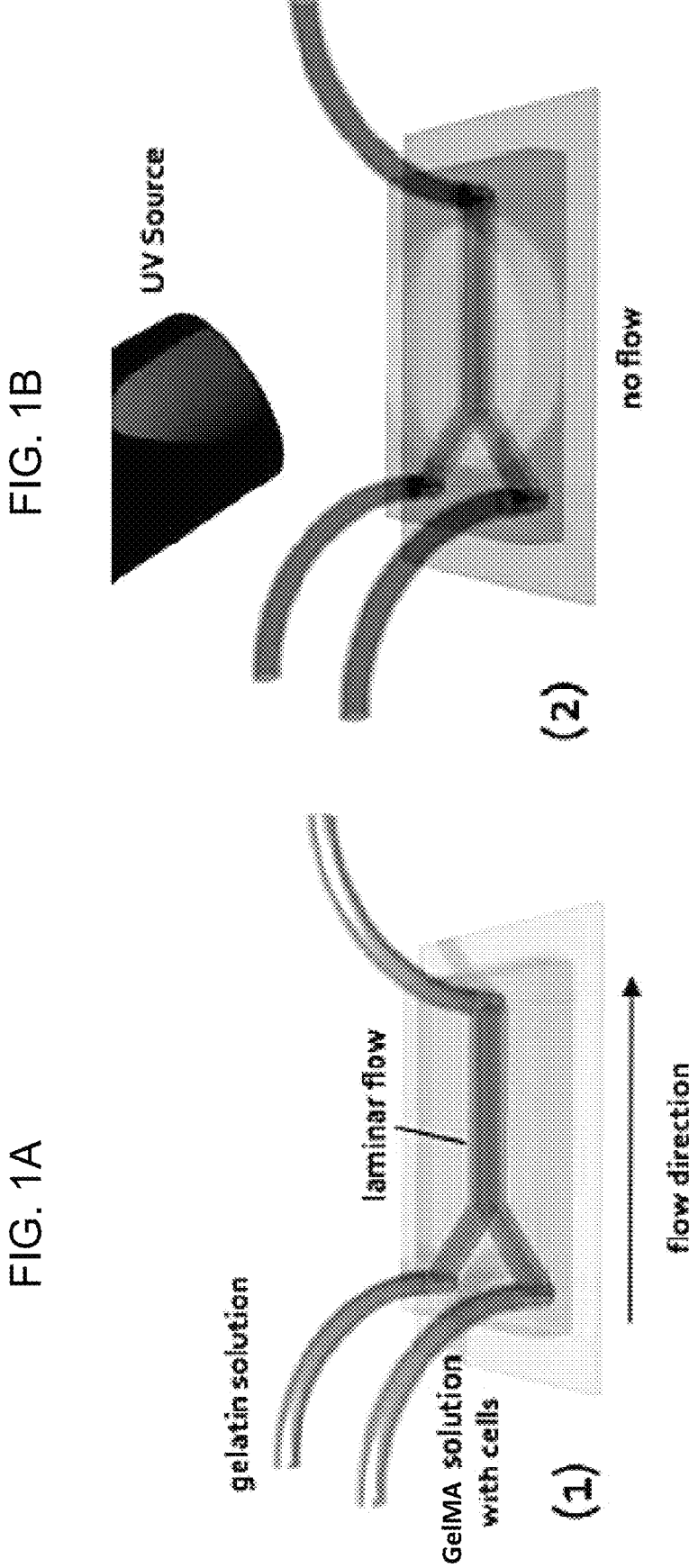
FIG. 1 is an embodiment of the fabrication of a tissue barrier according to the present disclosure utilizing stop-flow polymerization.

Described below are various embodiments of two-dimensional models of tissue barriers, methods of making and using the same, and on-model analysis techniques. Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

DISCUSSION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medical imaging, physics, mechanical engineering, biochemistry, cellular biology, cancer biology and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

It is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DESCRIPTION

The present disclosure is directed to two-dimensional (2D) models of tissue barriers, methods of making and using the same, and on-model analysis techniques.

Described herein are embodiments of a Y-junction (or Y-channel) single-layer microfluidic device that can provide for the parallel flow of two or more solutions. One solution of the two or more solutions can be UV polymerized to form a solid scaffold and the other solution of the two or more solutions can continue to flow under UV light. The in-situ formation of the scaffold can enable controlled formation of tissue-on-chip. Devices and methods described herein represent a simple, direct, and novel method to model tissue barriers. Other systems utilize plastic membranes to separate types of cells in culture. Devices and methods as described herein remove any need for a barrier material, which results in a more physiologically relevant and viable system. For operation, fluid can be pumped through the open channel while the polymerized half remains intact. Cells (such as endothelial cells or human umbilical vein endothelial cells, HUVECs, for example) can be introduced to the open channel and can adhere to the side of the polymerized scaffold to form a vasculature-like barrier. Other cell types can also be trapped inside the 3D polymerized scaffold, interacting with the endothelial layer without semi-permeable membranes blocking interface. Antagonists or agonists (small molecules, peptides, nucleic acids, etc) can be perfused through the open channel to assess the selectivity of the cell barrier under controlled stressors. Cell orientation and interactions can be imaged in real-time due to the 2D nature of the device, and electrodes can be incorporated to provide an electrical impedance map of the entire system.

Further improvements over existing systems include: simple fabrication, clear and real-time imaging Physiologically-correct microanatomy of blood barriers (i.e., cell interactions without membrane separation), cell exposure to physiological shear stress, and high-throughput manufacturing.

Methods and devices as described herein can have applications in pharmaceutical development, antagonist and chemical study on barrier integrity (vascular barrier integrity, for example), re-time measurement of barrier development or degradation, and the close study of cell-cell interactions in a dynamic environment. Regarding pharmaceutical development, devices and methods as described herein can aid in potential novel therapeutic compound development and testing (novel compounds such as small molecules, peptides, or nucleic acids, for example), either complimenting or circumventing non-human animal testing.

Tissue barriers as described herein can comprise a layer of cells, for example endothelial cells. At the tissue barrier can be an interface where another cell type, for example neurons or glia, interact with the tissue barrier.

As used herein, a model can be a tissue model or microphysiological model (MPM) which can represent a dynamic microenvironment that can recapitulate the physiology and geometry of complex organ system. An example of a model of a complex organ system as used herein is the neurovascular unit, which forms the makeup of the blood-brain barrier, and comprises the interaction (physical, chemical, and/or electrical) of glia (microglia and astrocytes, for example), neurons, endothelial cells, pericytes, and the basement membrane.

As used herein, a cell or cell type can be any cell derived from any one of the endoderm, endoderm, or mesoderm. In certain aspects, a cell can be an endothelial cell, a neuron, or a glial cell. A cell type can be an endothelial cell type, a neuronal cell type, or a glial cell type.

Methods of Making Tissue Models

Described herein are embodiments of methods of making a tissue barrier according to the present disclosure. According methods as described herein, a microfluidic device is provided. A microfluidic device can be a y-junction type device with a first and second input channel that converge into a flow or monitoring channel (see discussion above and drawings) with an output channel. A first solution can be introduced into the first input channel of the microfluidic device. A second solution can be introduced into a second input channel of the device. The first and second solution can be allowed to flow into the flow channel of the device utilizing passive flow, laminar flow, and/or flow driven by one or more fluid pumps. The flow can then be stopped and a polymerization method applied to the device, in particular the flow channel where the first and second solution are mixed. Flow of a third solution in the first input channel, second input channel or both can then be activated and the flow stopped to allow components of the third solution to adhere to aspects of the flow channel.

The first solution can be a non-polymerizing solution and the second solution can be a polymerizing solution.

The first solution can be a non-polymerizing solution. The first solution can comprise a cell-adherent coating. The non-polymerizing solution can be biocompatible and of comparable viscosity to the polymerizable solution. The first solution can be comprised of poly-ethylene glycol (PEG), gelatin, or phosphate-buffered saline (PBS). In an embodiment, the non-polymerizing solution is gelatin.

The second solution can be a polymerizing solution. The second solution can comprise a photopolymerizable hydrogel. Any photocurable polymer scaffold can be appropriate as a component of the polymerizing solution, including other gelatin-methacryloyl (GelMA), PEG derivatives (for example PEG-thiol), methacrylated collagen, or composite materials that will polymerize with exposure to a light source in a defined range. Weight percent of these components can be dependent on application, as the scaffold must have enough solids to form a complete scaffold, yet remain porous similar to extracellular matrix in order for cells or organize in 3D. In an embodiment, the polymeric scaffold is a GelMA composite scaffolds, ranging between 4-10% solids. The second solution can further comprise a photoinitiator, for example Irgacure® 2959 and lithium phyenyl(2, 4,6-trimethylbenzoyl)phosphinate. Other suitable photoinitiators can be used that are known in the art by the skilled artisan. In embodiments, the photoinitiator can be present in amount of about 0.4% to 0.6% by weight. In an embodiment, the photoinitiator can be present in an amount of about 0.5% by weight. In an embodiment, the photoinitiator is 0.5% Irgacure® 2959.

The first solution can be passed into the flow channel through the first microfluidic input channel and the second solution passed into the flow channel through the second microfluidic input channel. The relative flow rates of the two respective inlets for the two channels can be about 1:100 to 100:1. Flow rates can vary at many ratios to achieve the desired scaffold and vessel size. Appropriate flow rates for fabrication do not have to fall within a defined range because the flow is stopped in order to polymerize under UV. Flow can be undertaken as to achieve half of the flow channel filled with scaffold solution (i.e. polymerizing or polymerizable solution) and the other half non-polymerizing solution.

Flow according to the method can be laminar flow.

The first solution, second solution or both, can comprise a first plurality of cells. The first plurality of cells can be comprised of endothelial cells or fibroblasts, individually or in combination. The endothelial cells can be mammalian umbilical vein endothelial cells or brain endothelial cells, in particular human cells. Fibroblasts can also be mammalian.

Components of the third solution can be a second plurality of cells. The second plurality of cells can be a singular cell type or a mix of cell types. The second plurality of cells can comprise neurons and glia. The second plurality of cells can be mammalian. In an embodiment, the second plurality of cells can be neurons and astrocytes. In an embodiment, the second plurality of cells can be neurons, astrocytes, and microglia.

Tissue Models

A tissue model can comprise a first microfluidic input channel and a second microfluidic input channel. These channels are in fluidic communication with and converge in a microfluidic flow channel (also referred to herein as a monitoring channel), which is configured to receive flow from the first microfluidic input channel and second microfluidic input channel. An output channel is configured to receive flow from the microfluidic flow channel and output solutions from the tissue model. An array of electrodes can be embedded in the tissue model and configured to monitor (or map) electrical impedance of the flow channel. The first and second microfluidic input channels can further comprise a first conduit and a second conduit that are configured to introduce fluids into the first and second microfluidic input channels. The tissue model can further comprise a base in which the first and second microfluidic input channels and microfluidic flow channel can be created by a method such as lithography.

Channels of the tissue models as described herein can be fabricated in widths, including but not limited to, of 100 micrometers to 1000 micrometers, although the skilled artisan would understand that channel widths can be beyond this range according to additional factors including desired application. In embodiments, channel width is 100 micrometers to 1000 micrometers. In an embodiment, a channel is 500 micrometers wide.

The tissue model can comprise about 6 to about 180 electrodes configured for impedance monitoring of the flow channel, depending on the desired density of data along the flow channel. In an embodiment, the tissue model comprises 60 electrodes. The electrodes can be configured as electrode pairs. The spacing or distance between electrodes can range depending on the desired application and size of the channel.

Electrodes can be about 5 microns to about 100 microns in diameter, depending on factors such as channel size. In an embodiment, the electrodes are 50 microns in diameter.

Electrodes as described herein can be of a variety of materials as long as the material is conductive. In embodiments according to the present disclosure, the electrodes can be Ag, AgCl, poly(3,4-ethylenedioxythiophene) (PEDOT), indium tin oxide (ITO), chromium, and gold, individually or in combination.

Tissue models as described herein can further comprise a polymeric scaffold on one or more surfaces of the flow channel. In certain aspects, the polymeric scaffold can coat the entirety of the surfaces of the flow channel. The polymeric scaffold can be a UV-polymerized scaffold. The polymeric scaffold can be comprised of one or more of GelMA, PEG derivatives, methacrylated collagen. The polymeric scaffold can further be comprised of poly-ethylene glycol (PEG) and gelatin.

Tissue models as described herein can comprise a first plurality of cells cultured on, adhered to, or embedded within the polymeric scaffold. The first plurality of cells can be comprised of endothelial cells. The first plurality of cells can be a mammalian endothelial cell, for example human or rodent. In an embodiment, the first plurality of cells is a HUVEC, hBMVEC, or fibroblast, individually or in combination. In an embodiment, the first plurality of cells are HUVECs. In an embodiment, the first plurality of cells are hBMVECs. In an embodiment, the first plurality of cells are fibroblasts.

Tissue models as described herein can further comprise a second plurality of cells, different than the first, cultured on (or adhered to) the first plurality of cells, polymeric scaffold, or both. In embodiments, the second plurality of cells comprise neurons and astrocytes cultured on the endothelial cells. In embodiments, the second plurality of cells comprise neurons, astrocytes, and microglia cultured on the endothelial cells.

While embodiments of the present disclosure are described in connection with the Examples below and the corresponding text and figures, there is no intent to limit the invention to the embodiments in these descriptions. On the contrary, the intent is to cover all alternatives, modifications, and equivalents included within the spirit and scope of embodiments of the present disclosure.

EXAMPLES

Example 1

The present example discloses an embodiment of a method of the fabrication of a tissue barrier according to the present disclosure, and an embodiment of the tissue barrier.

Figures 1C, 1D:
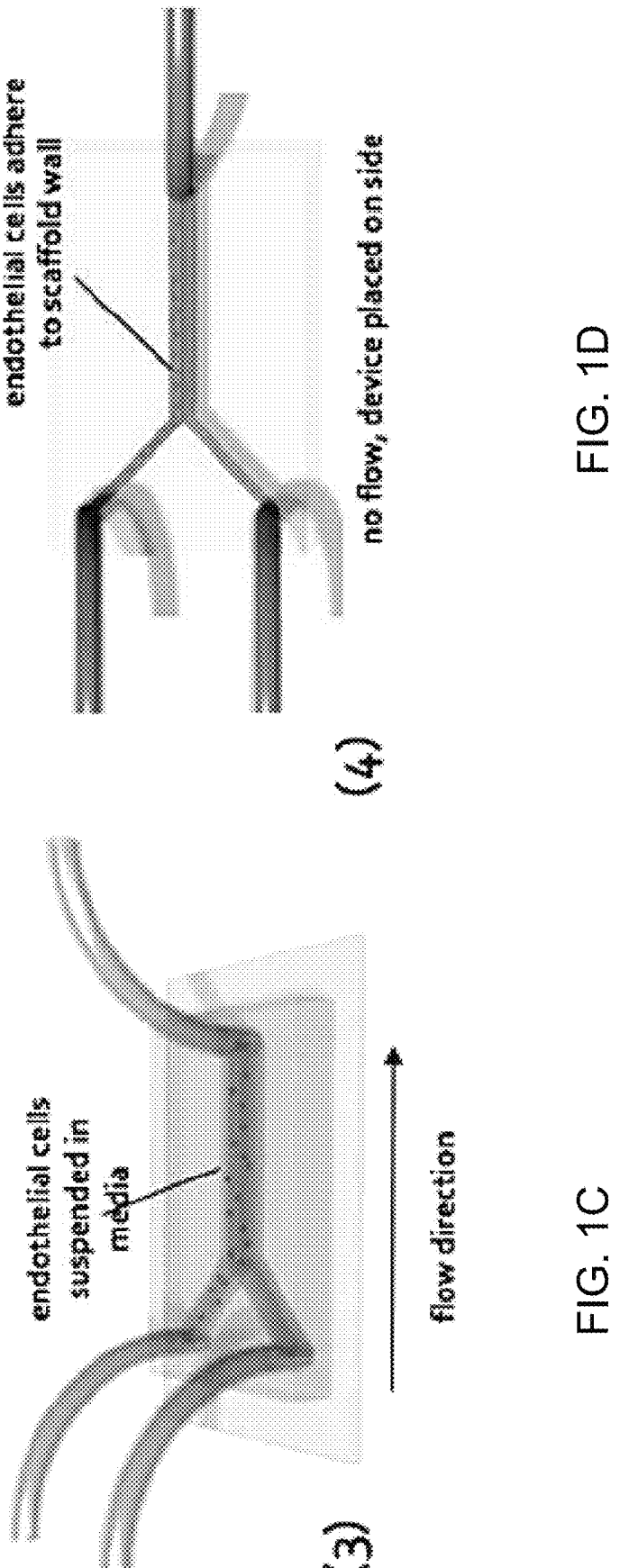
Figure 1E:
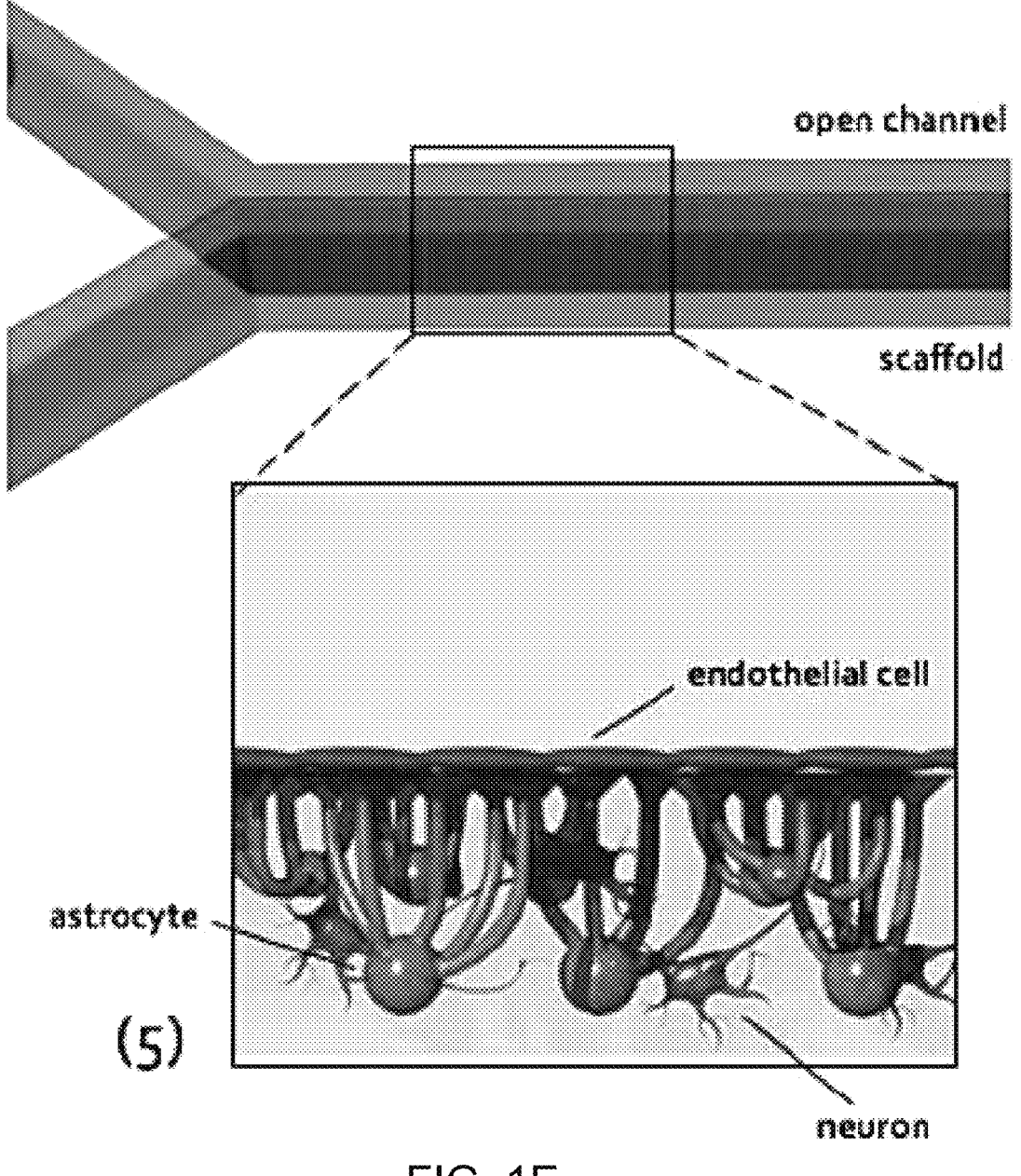

According to the present example, FIGS. 1A-1E illustrate an embodiment of the fabrication of a tissue barrier according to the present disclosure. As can be seen in FIG. 1A, a gelatin solution flows in one channel of a y-shaped channel toward the junction, and a GelMA solution with cells flows through the other channel via laminar flow. After the contents of the channels meet at the junction and flow into monitoring portion of the device (where they can be mixed), flow is then stopped. After flow is stopped, the scaffold material is polymerized with, for example, a light source (FIG. 1B). Following polymerization the cells (for example endothelial cells) can adhere to the polymerized scaffold (FIGS. 1C-1D). Additional cell types (for example neurons and glia, astrocytes, pericytes, or microglial) can be fed into the system that can adhere to the scaffold and/or endothelial cells and be co-cultured in the device (forming a model of the neurovascular unit that makes up the blood-brain barrier in this example)(FIG. 1E).

Figure 2:
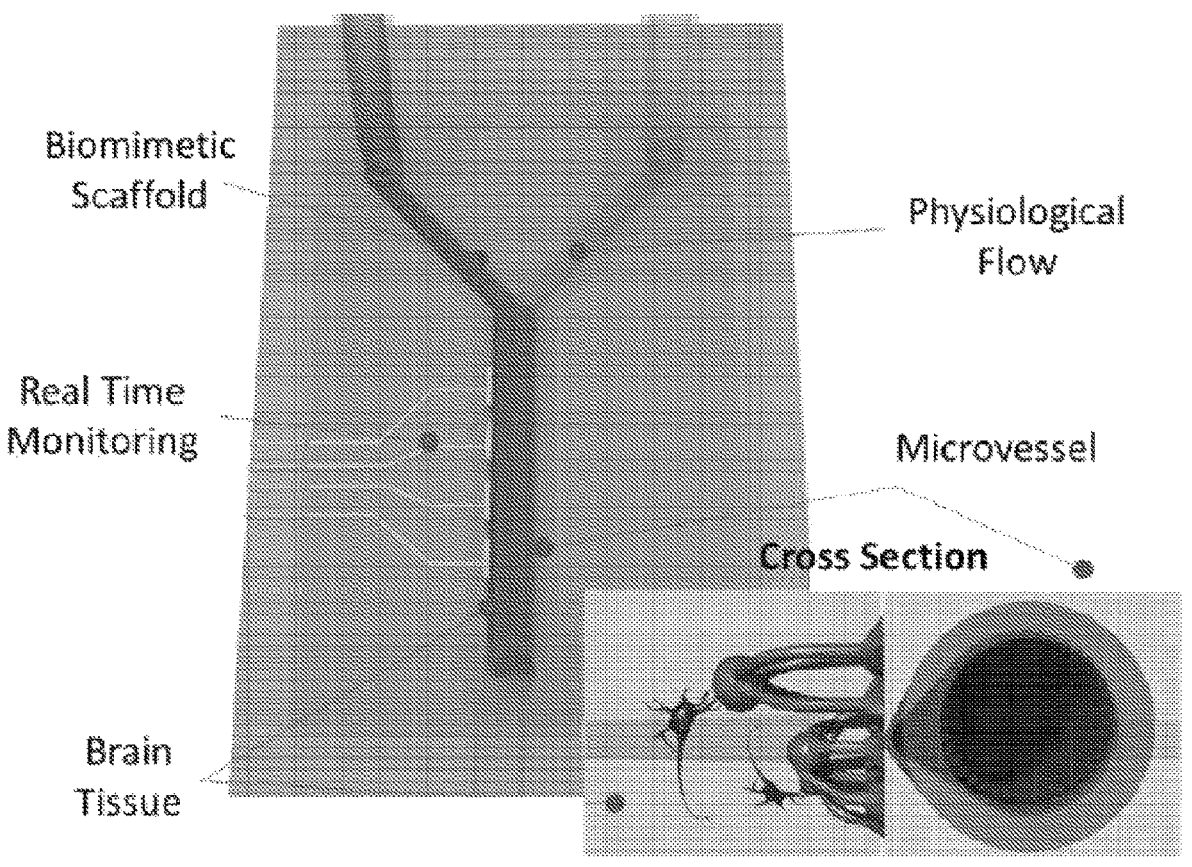
FIG. 2 is an embodiment of a biomimetic scaffold according to the present disclosure.

FIG. 2 is an embodiment of a biomimetic scaffold according to the present disclosure. Aspects of systems and methods as described herein are shown in FIG. 2, for example a biomimetic scaffold, physiological flow, real-time monitoring, and a model of the neurovascular unit (i.e. unit forming the blood-brain barrier or brain tissue). The inset shows the circular cross-section of the monitoring portion of the device with the scaffold polymerized and cells adhered in a co-culture configuration. Although the neurovascular unit/ blood brain barrier is shown in the present example, it is to be understood that other tissue barriers (vascular-endothelial barriers, especially) can be modeled according to systems and methods as described herein.

Figure 3:
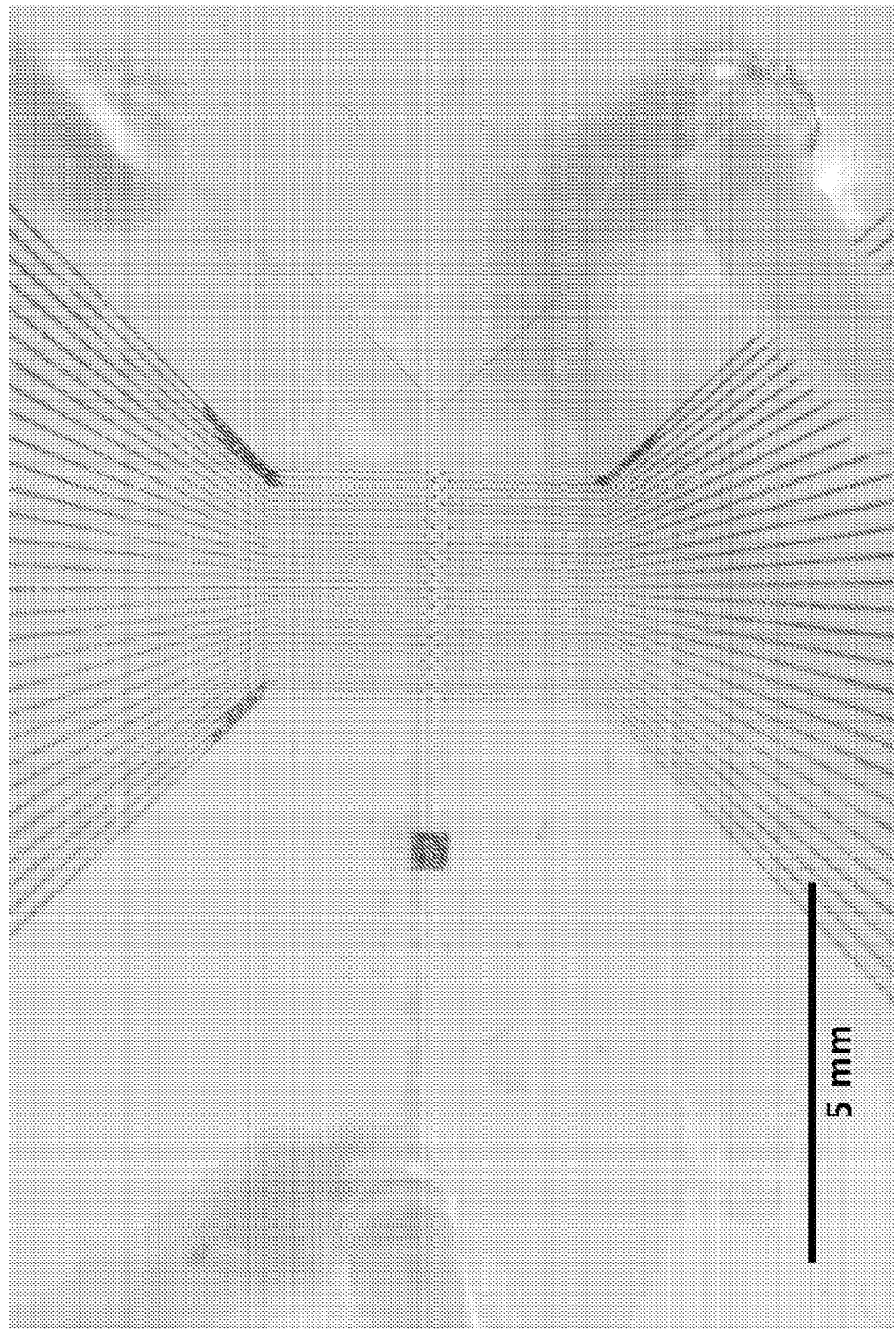
FIG. 3 is a photograph showing operation of an embodiment of a Y-channel tissue barrier model with integrated barrier monitoring electronics according to the present disclosure.

FIG. 3 is a photograph showing operation of an embodiment of a Y-channel tissue barrier model with integrated barrier monitoring electronics according to the present disclosure.

Figure 4:
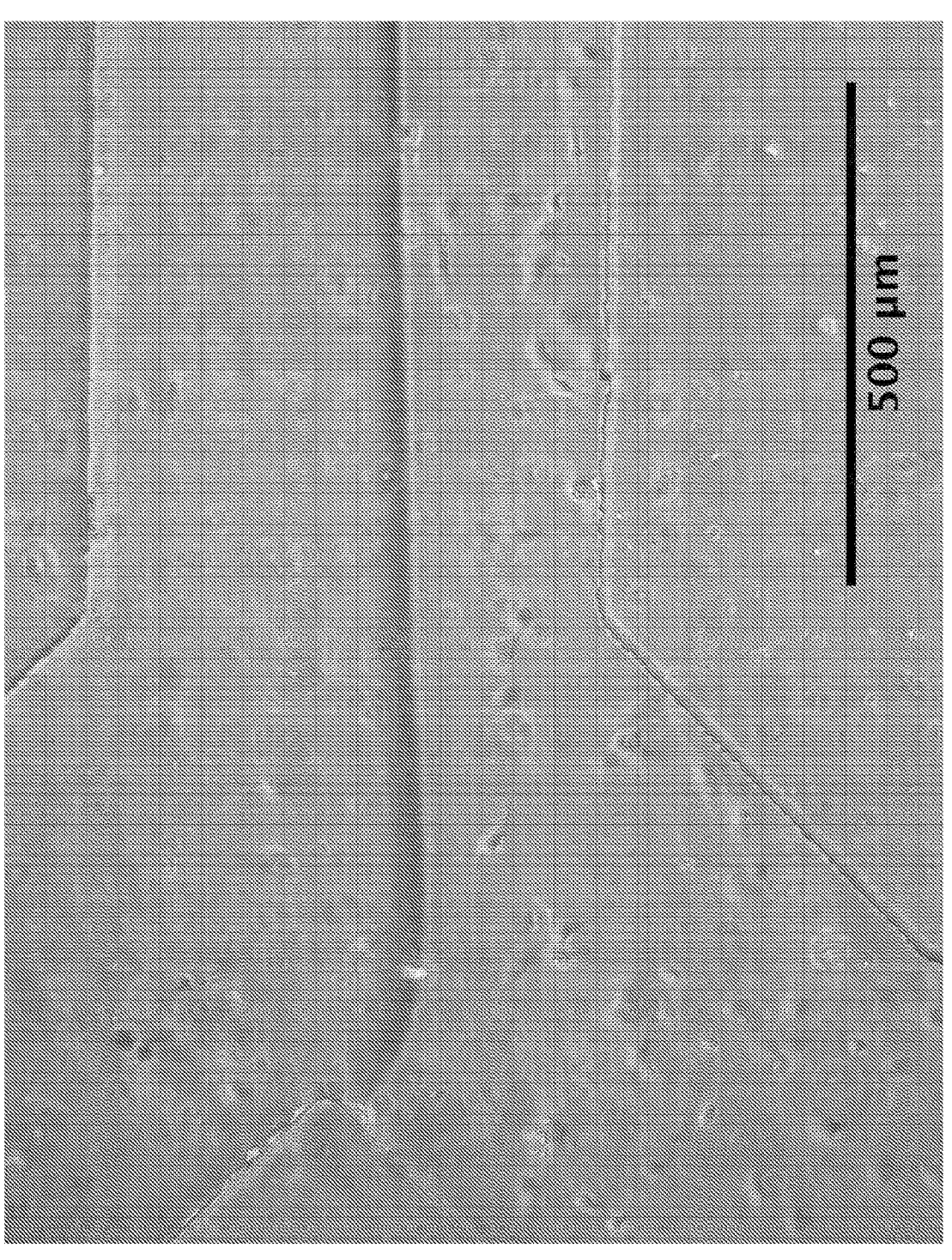
FIG. 4 is a micrograph of an embodiment of a Y-channel tissue barrier model showing inlets and human cells in culture according to the present disclosure.

FIG. 4 is a micrograph of an embodiment of a Y-channel tissue barrier model showing inlets and human cells in culture according to the present disclosure.

Figure 5:
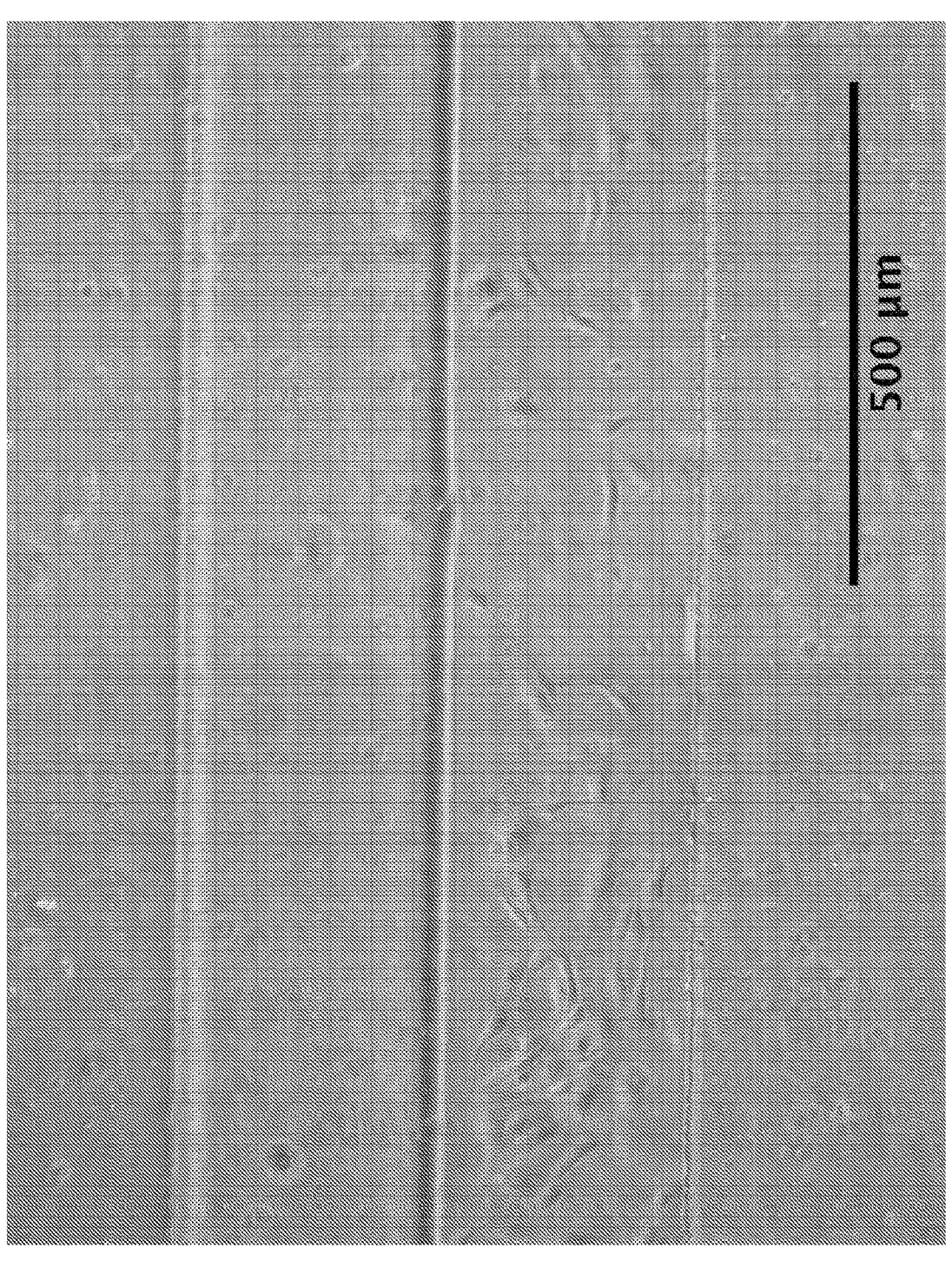
FIG. 5 is a micrograph of an embodiment of a Y-channel tissue barrier model showing center of barrier and human cells in culture according to the present disclosure.

FIG. 5 is a micrograph of an embodiment of a Y-channel tissue barrier model showing center of barrier and human cells in culture according to the present disclosure.

Figure 6:
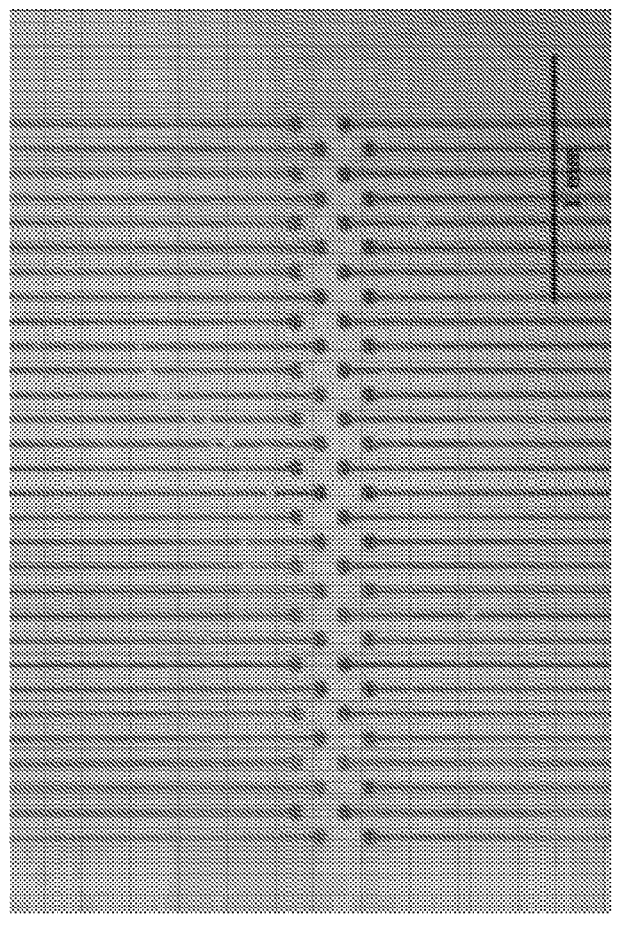
FIG. 6 is a micrograph of an embodiment of an integrated barrier monitoring electronics according to the present disclosure.

FIG. 6 is a micrograph of an embodiment of an integrated barrier monitoring electronics according to the present disclosure.

Example 2

Vasculature-Tissue Interfaces

Figure 7:
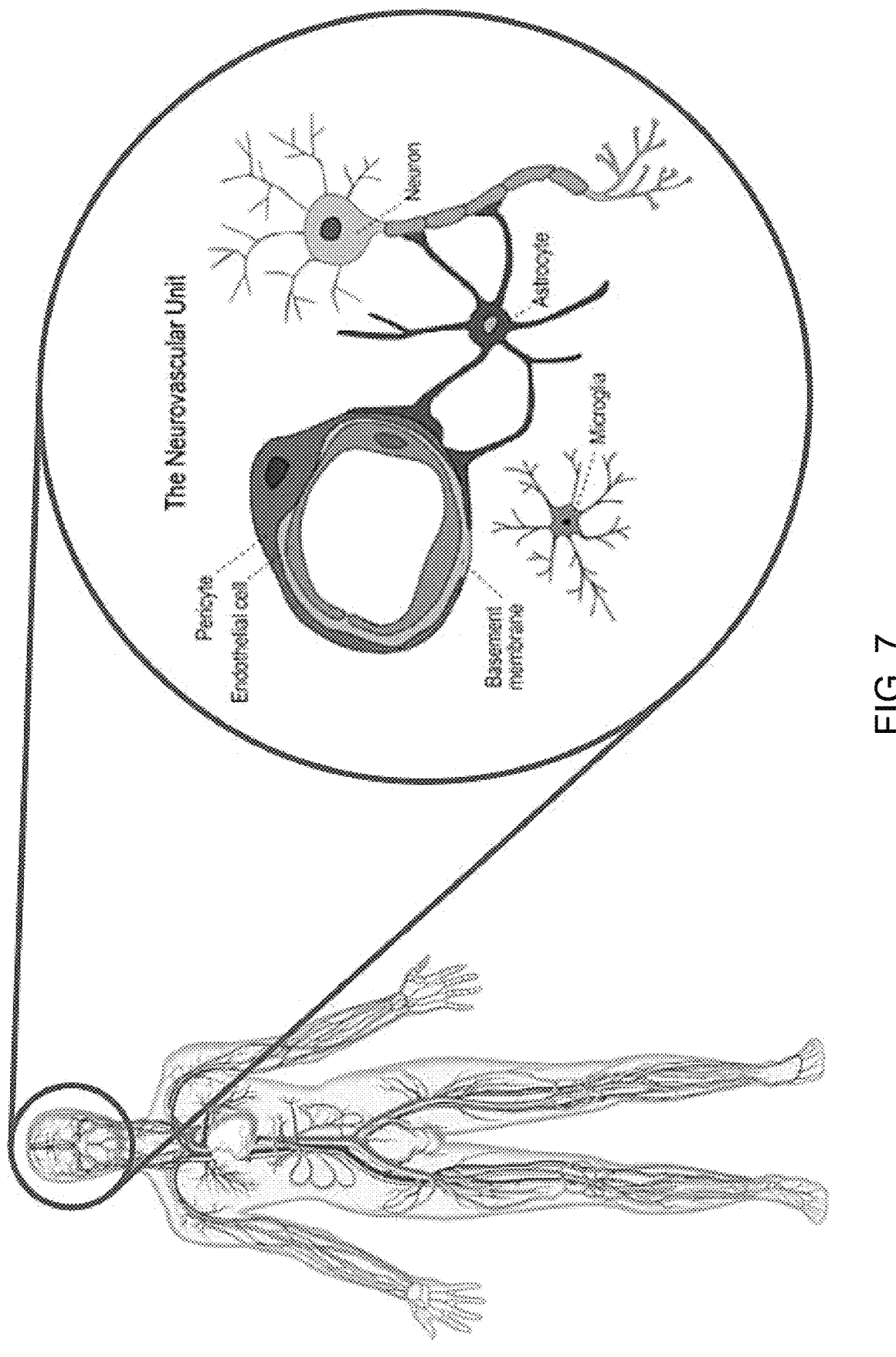
FIG. 7 is an illustration of the neurovascular unit, a component of the blood-brain barrier, an example of a dynamic microenvironment that can be modeled by devices and methods as described herein.
Figure 9:
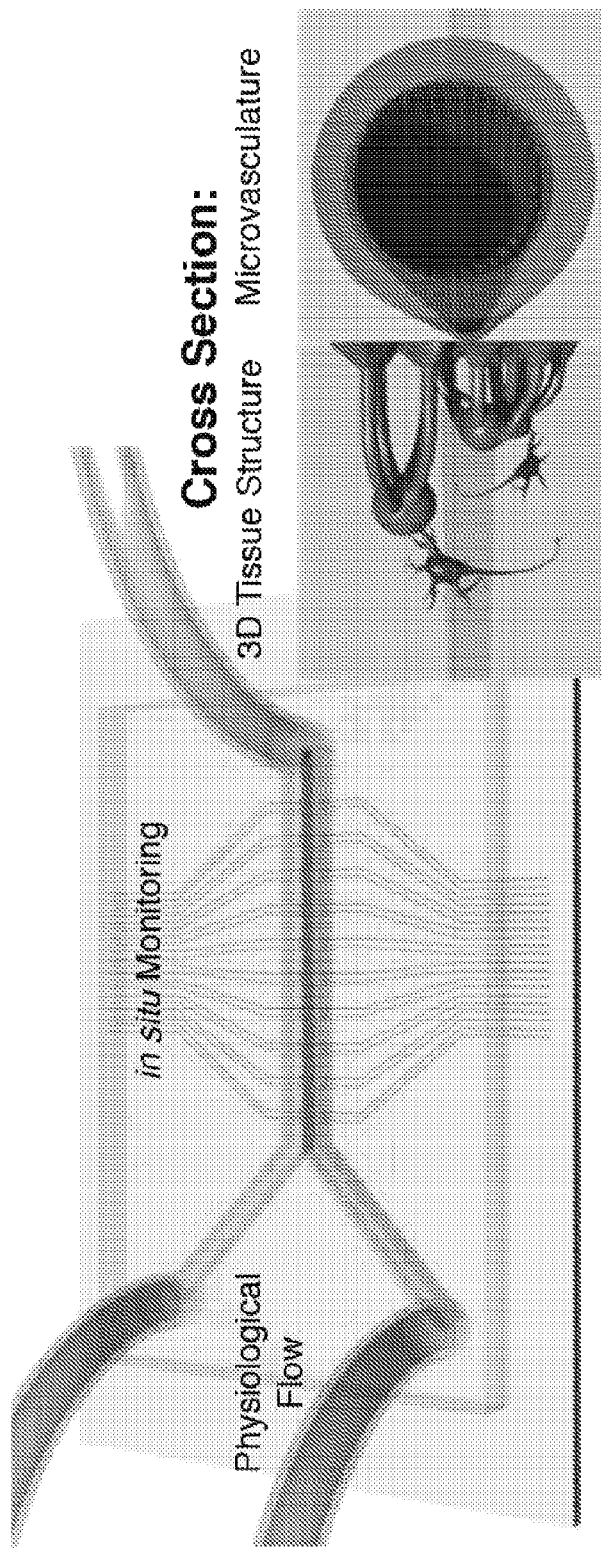
FIG. 9 is an illustration of an embodiment of a tissue model as described herein. A model of a vasculature-tissue interface can be created within a y-channel (or y-junction) microfluidic device with stop-flow polymerization.

The Blood-Brain Barrier (BBB) is the most selective tissue barrier in the body, predominately operating via active transport of nutrients and waste products, while maintaining a chemically stable brain environment and protecting the central nervous system (CNS) from harmful substances. Composed of endothelial cells, glial cells, and neurons, the BBB separates the circulatory system from the CNS. Dysfunction or disruption of the BBB plays a major role in many pathologies; nonetheless, proper function of the BBB is also a major roadblock for drug and therapy development, restricting treatment options for said neuropathologies. Animal models are often utilized to study transport across the BBB, though results lack predictive power due to functional differences across animal and human responses. Transwell® models with human cells used as a precursor to animal studies demonstrate poor barrier selectivity arising from a lack of necessary cell phenotypes dependent on fluid flow. There is critical need for an in vitro model that recapitulates relevant functional responses to further both fundamental biological studies and biotechnology development, i.e. drug development and tissue engineering. Microphysiological models (MPMs) are microdevices that mimic a specific tissue function, incorporating physiologically relevant microanatomy, mechanics, and cell types, such as those of the blood brain barrier (FIG. 7, an embodiment of a tissue model of the present disclosure shown in FIG. 9). The application of vasculature-tissue barriers in MPMs is expansive, especially as a platform for exploratory studies in developmental biology, pharmaceutical design, and drug delivery. Conceptually, providing the appropriate environment results in cell organization, communication, and operation as in vivo, therefore creating a benchtop device with the functionality of a living organism. In practice, existing MPMs of the BBB are incomplete due to limited microfabrication and microanalysis techniques.

Current Vasculature Tissue Devices

The BBB has been explored using both in vivo and in vitro models. In vivo animal models are complex, low throughput, and expensive. Although animal models offer a wealth of information regarding disease states and developmental biology it is difficult to draw conclusions on single biological phenomena due to myriad confounding variables. To better inform animal models, in vitro models with fewer variables have been developed. Current in vitro models have the following pitfalls: lack of flow present in real vessels and incomplete cell interactions necessary in the BBB. A common in vitro technique is to culture different cell types on either side of a Transwell, often to facilitate communication between endothelial cells and astrocytes. Shear stresses and constant nutrient perfusion are absent in this model, but necessary for proper barrier development and interaction. To combat this issue, many research teams have designed microphysiological models (MPMs) to mimic the BBB. Although incorporating flow, current BBB-MPMs are still limited by a semi-permeable membrane, single cell types, or 2D cell culture. This is not ideal for many reasons, first being that they can be difficult to assemble, requiring precise alignment and layering of multiple components which is user intensive and time consuming, suggesting such devices would not be realistic for industry use. MPMs have immense value in the pharmaceutical industry for high throughput drug testing. This is currently limited because devices must be sacrificed and analyzed post facto, requiring a separate device at single time points for all conditions. There is a need for a MPM that recapitulates organ systems without requiring intensive and low-throughput analysis.

Measuring Permeability in MPMs

Figure 8:
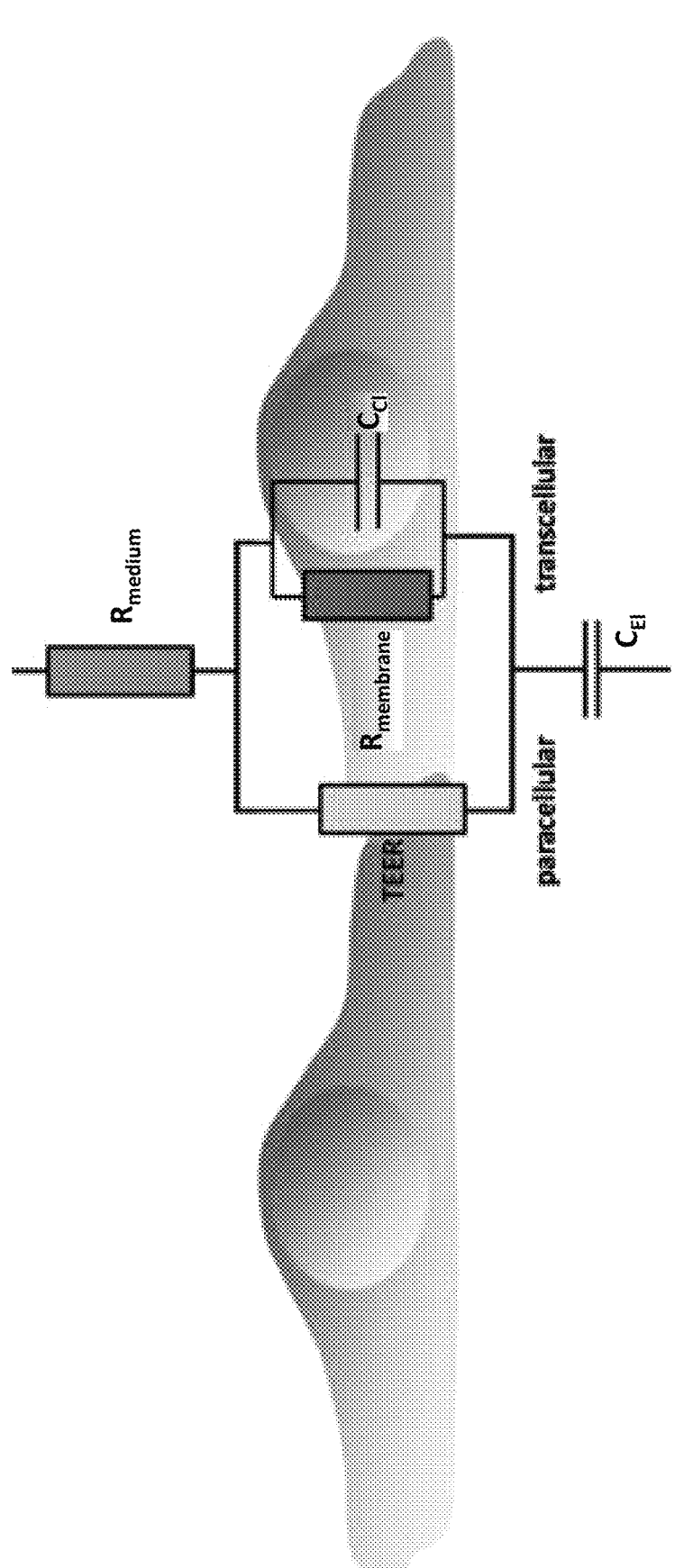
FIG. 8 is an illustration of a circuit model for mapping transendothelial electrical resistance according to devices and methods as described herein.

Permeability can be quantified by determining the flow of electrical current through a barrier. Barrier resistance can be directly correlated to transport of solutes through a system. Low resistance across a barrier is indicative of a more permeable system. A common way to monitor barrier development is by measuring the transendothelial electrical resistance (TEER; FIG. 8). TEER is defined by the following equation, with the terms TEER ($\Omega \cdot cm^2$), $R_{barrier}$ ($\Omega$), and A ($cm^2$):

$$TEER = R_{barrier}(Area) \tag{Eq. 1}$$

The resistance of the barrier ($R_{barrier}$; in $\Omega$) is measured by driving a current (I) across the Transwell, typically with a 12.5 Hz square wave. The resultant voltage (V) is measured, and using Ohm's law (R=V/I), the Ohmic resistance is determined. There are many disadvantages to validating systems based on TEER. These measurements often have high variability due to inconsistent electrode position and non-uniformity of current density across the barrier. The electrodes must be placed directly above and below to the barrier to drive current through the membrane perpendicular to cell growth. Furthermore, the electrodes must also be the same shape and size as the membrane to assure the current path is consistent. When these conditions are unmet, TEER is often reported falsely high. Furthermore, variations in environmental conditions, such as temperature and membrane nonuniformities, can create high variability in reported TEER. TEER measurements also provide limited information on barrier characteristics. Single frequency TEER is restricted to characterizing holes in barrier coverage i.e. where the cell culture is incomplete due to large, leaky gaps in the cell layer. Additionally, when measuring impedance in small channels, overwhelming media and tissue resistances will decrease the signal-to-noise ratio, making systemic changes more difficult to detect.

Vasculature-Tissue Microphysiological Model

Better than measuring TEER to characterize a MPM, impedance can be mapped along the entirety of microfluidic flow channels according to the present disclosure. Impedance analysis includes information on the phase angle between the applied current and resultant voltage in addition to magnitude. Therefore, capacitive characteristics of a system can be explored by collecting measurements across a frequency range. Low frequency measurements (200 Hz-5 kHz) provide information on resistive properties of a system, while high frequency (>10 k) outputs offer insight on capacitive properties. These measurements provide valuable information on the capacitance of the cell layer, cytoplasm conductivity, and other important transcellular and paracellular characteristics. Capacitive measurements have been used to determine cell viability, differentiation, and endocytosis, though in this model it can be used to determine uptake and movement of particles through the BBB via active transport.

Tissue models as described herein incorporate novel photocurable biomaterials and low Reynolds number flow to precisely control tissue geometry in a microchannel. Tissue model fabrication work-flow as described herein (FIGS. 1A-1E) allows for the omission of semi-permeable membranes, cutting back on assembly time and user training. Omitting the membrane from the present devices also allows high resolution imaging, further improved by the vertical orientation of the vessel and tissue structure. Furthermore, removing the semi permeable membrane may also provide astrocyte-endothelial interactions, thereby creating a system that better recapitulates in vivo human cellular pathways and functions. Shear is precisely controlled using external pumps during culture and many devices can be cultured and tested in parallel to increase throughput. Quantification is enabled beyond microscopy and post facto biochemical techniques by incorporating real-time functional monitoring with an in-line electrode array. In-line monitoring allows real-time analyses during vasculature development and disruption, expanding MPM use in pharmaceutical settings.

An embodiment of fabricating a tissue model is as follows. The Y-device is fabricated by soft lithography. In situ tissue fabrication is achieved with a normal human astrocyte (NHA) suspension of 5 million cells per mL in 6 wt % GelMA/PEG-SH composite with 0.5% photoinitiator. A split laminar flow profile is achieved by maintaining flow rates, stop-flow is initiated, and the device is exposed to UV light at 30 mW/cm2 for 5 seconds to polymerize the tissue structure. The non-polymerizing PBS solution in the residual open channel is replaced with astrocyte growth media (AGM). After 5-7 days of culture, the tissue structure begins to demonstrate cell morphologies indicative of healthy culture and proliferation (cell spreading, network formation, collagen secretion). Human brain microvascular endothelial cells (hBMVEC) are then introduced to the open channel at a density of about 5 million cells per mL. Y-devices are oriented on their side in the incubator to allow hBMVECs to adhere to the side of the tissue structure. Culture is maintained for 3-5 days, until a complete monolayer is formed.

Figure 10:
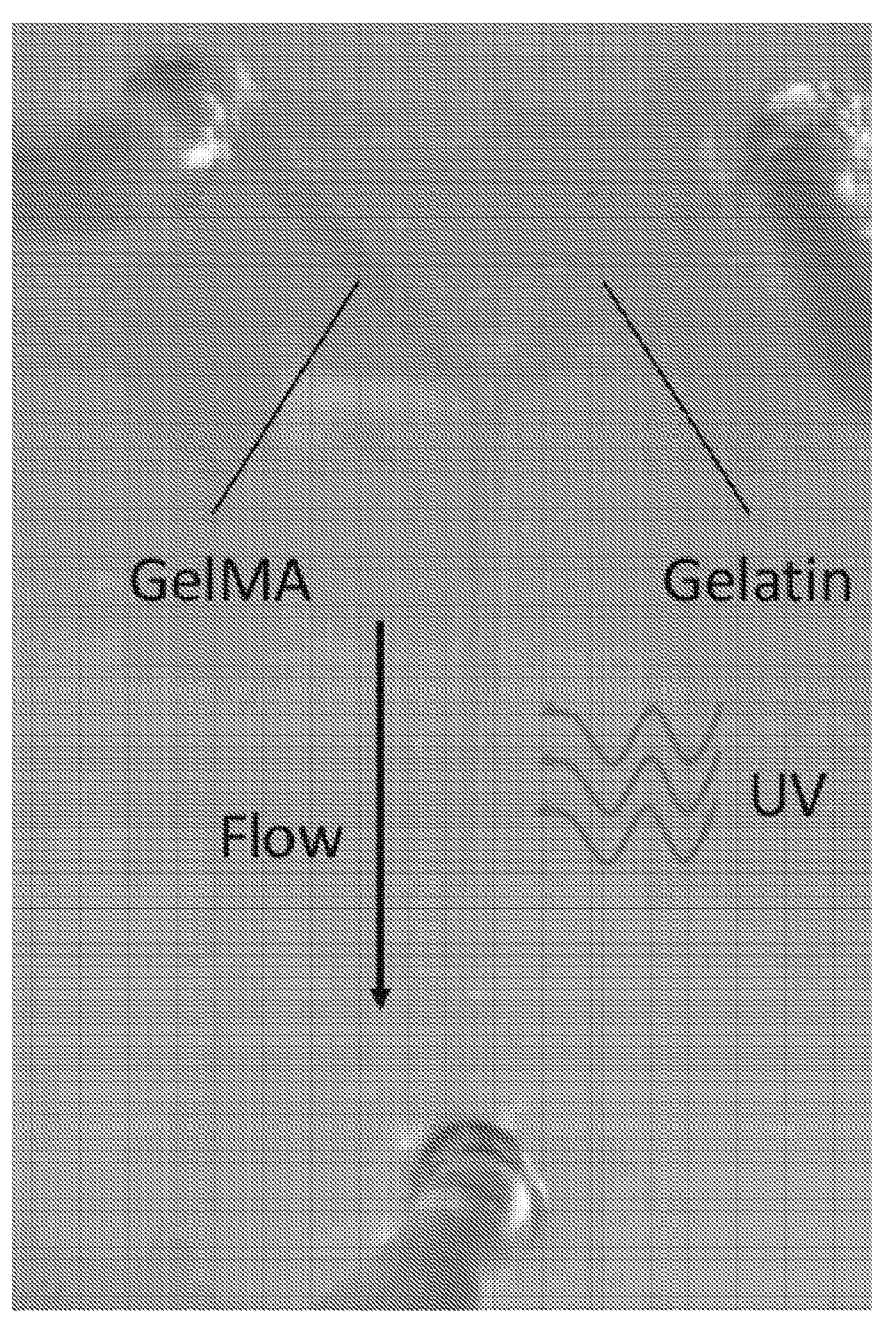
FIG. 10 illustrates an embodiment of polymeric scaffold creation according to the present disclosure. Gelatin and GelMA are allowed to flow into a channel, at which point flow is stopped. The mixture is then polymerized by the application of UV light.
Figure 11A:
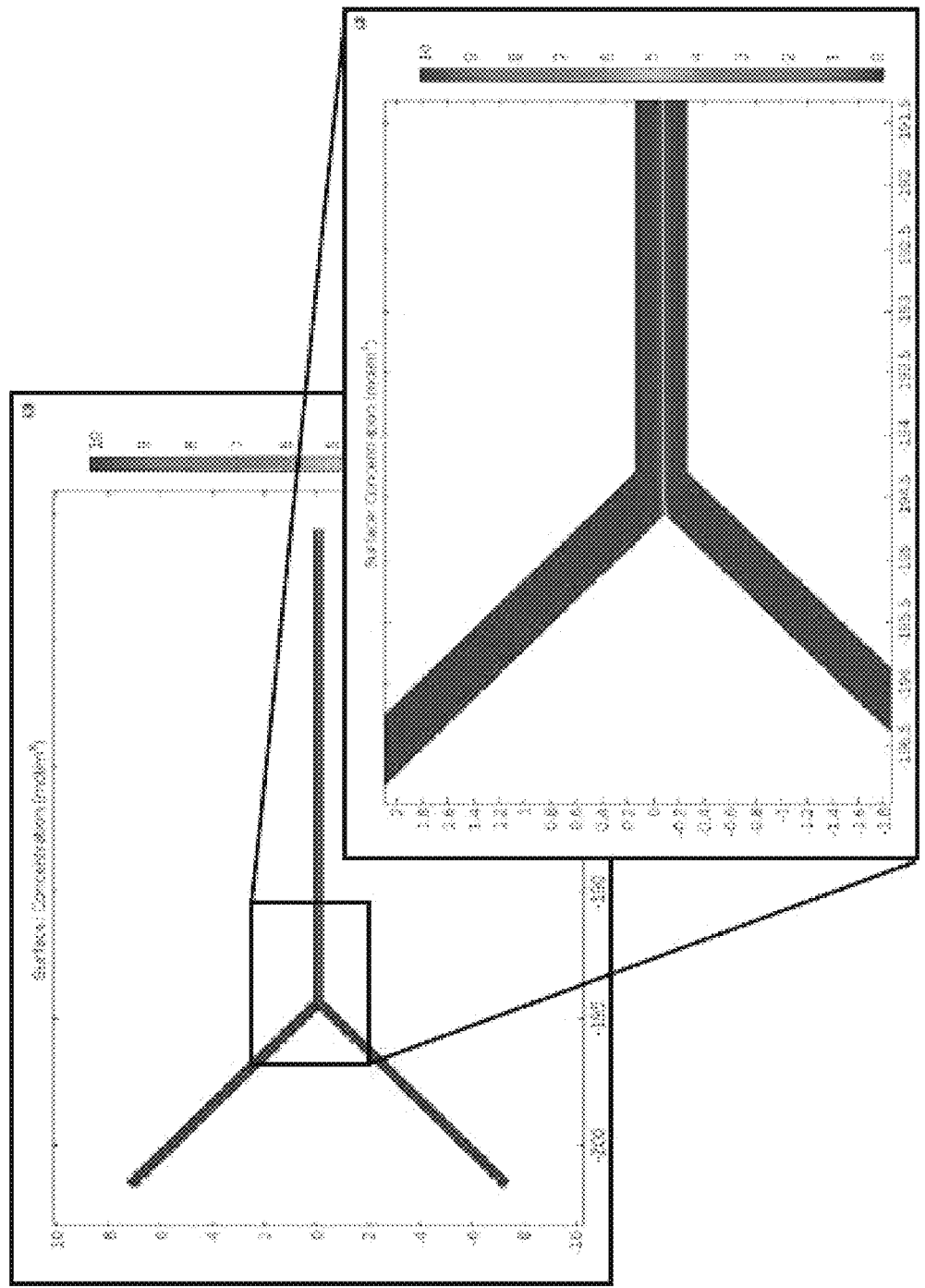
Figures 12A, 12B, 12C:
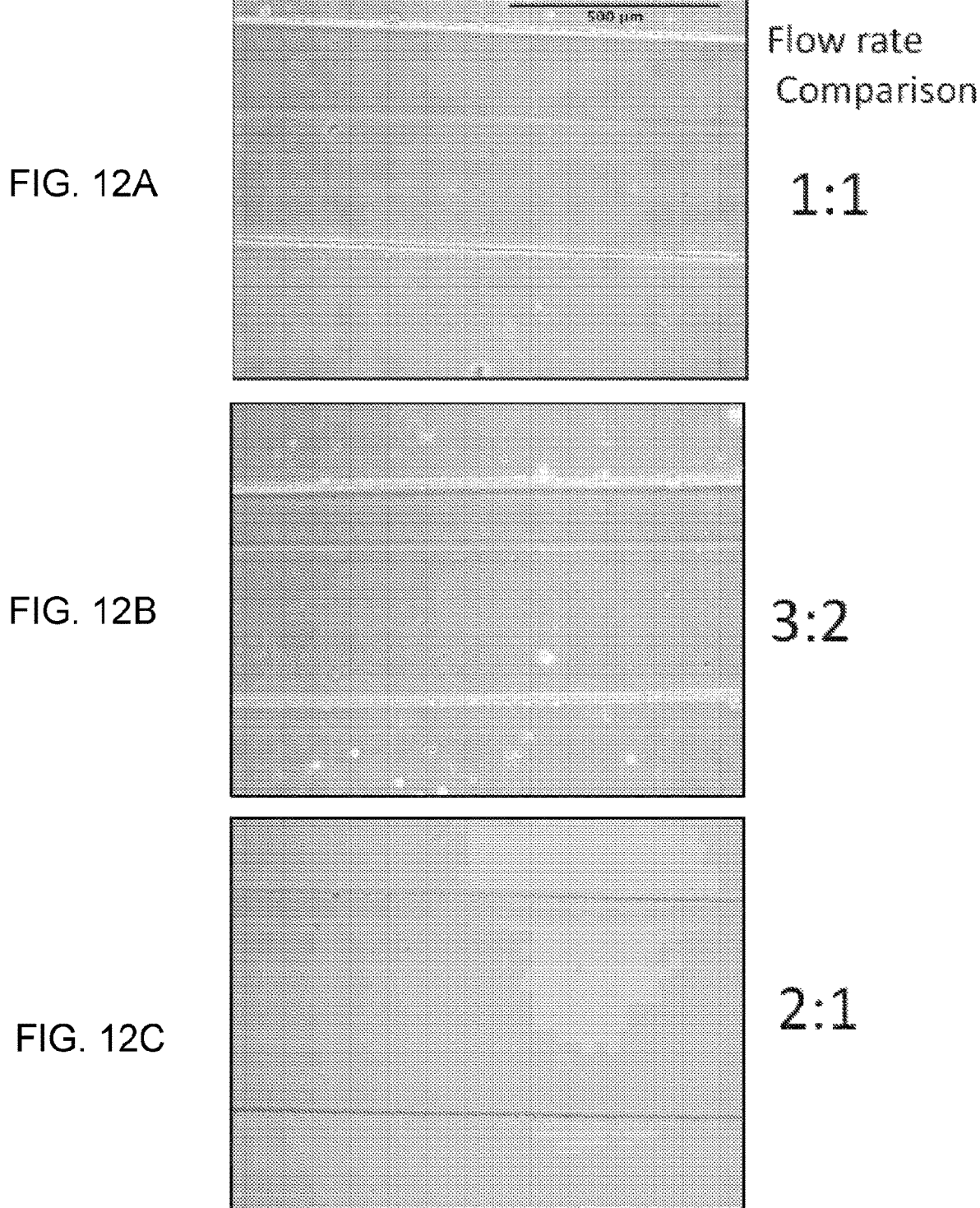
FIGS. 12A-12C are photographs of scaffold width in a channel, and comparison of flow rates.
Figures 13A, 13B, 13C:
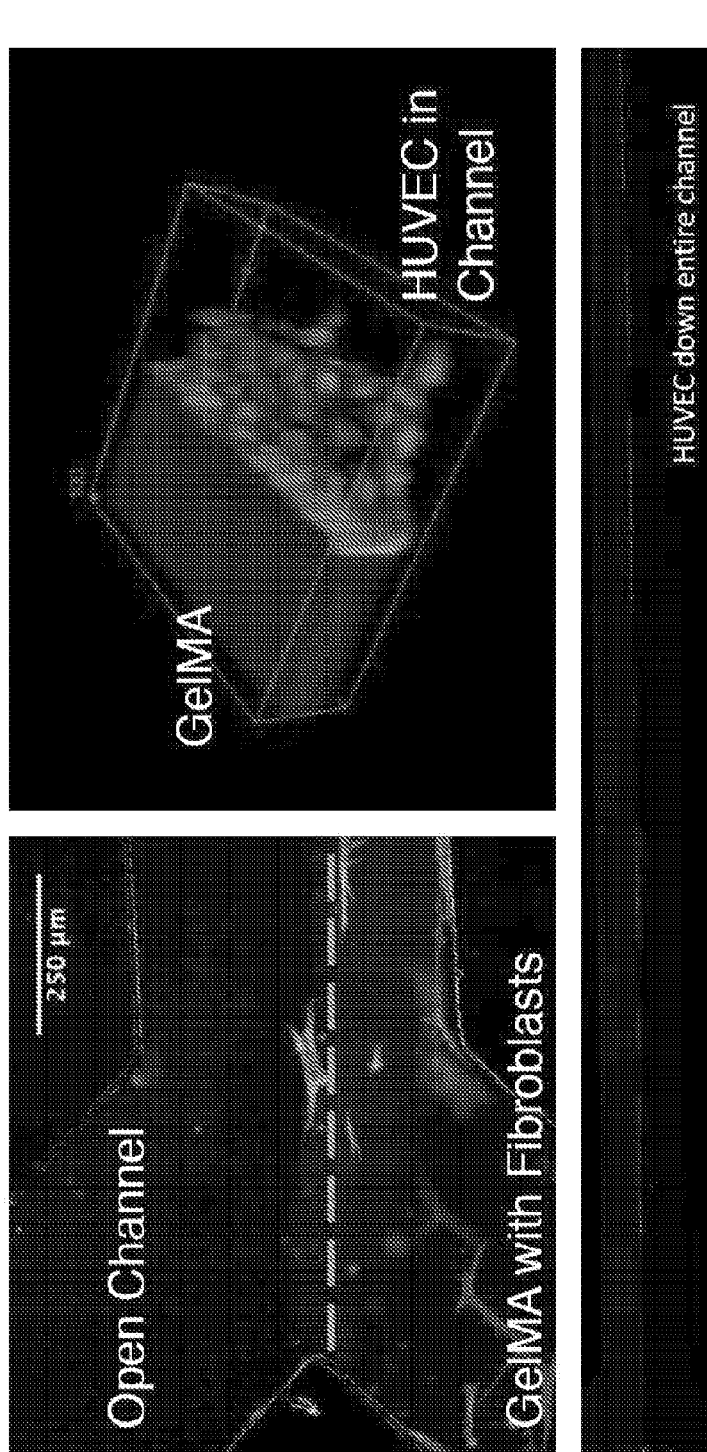
FIGS. 13A-13C are fluorescent micrographs showing GelMA with fibroblasts (FIG. 13A), GelMA with HUVEC in the flow channel (FIG. 13B), and HUVECs down the length of the entire flow channel (FIG. 13C).

FIG. 10 illustrates an embodiment of polymeric scaffold creation according to the present disclosure. Gelatin and GelMA are allowed to flow into a channel, at which point flow is stopped. The mixture is then polymerized by the application of UV light. FIGS. 11A-11B are maps and data showing scaffold swelling and thickness over time, and illustrating that laminar flow can control shape. FIGS. 12A-12C are photographs of scaffold width in a channel, and comparison of flow rates. FIGS. 13A-13C are fluorescent micrographs showing GeIMA with fibroblasts (FIG. 13A), GeIMA with HUVEC in the flow channel (FIG. 13B), and HUVECs down the length of the entire flow channel (FIG. 13C).

Impedance Mapping for In Situ Monitoring

Figure 14A:
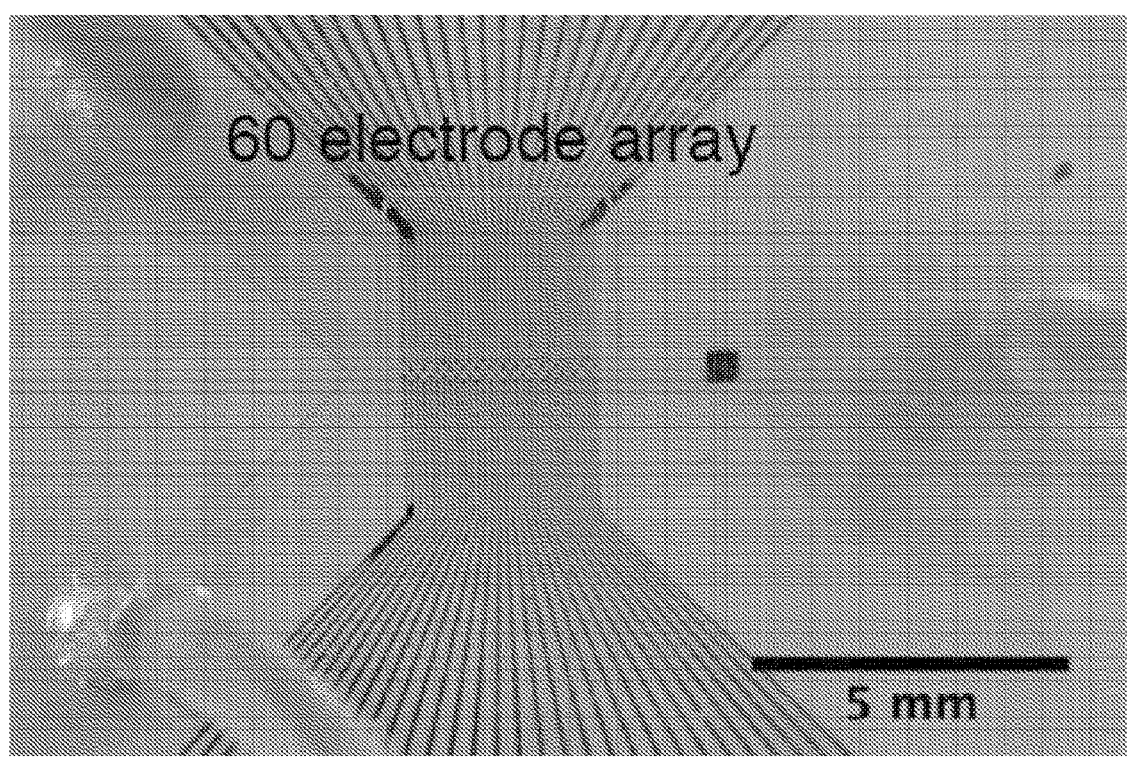
FIGS. 14A-14B are photomicrographs of an embodiment of aspects of tissue models as described herein.
Figure 14B:
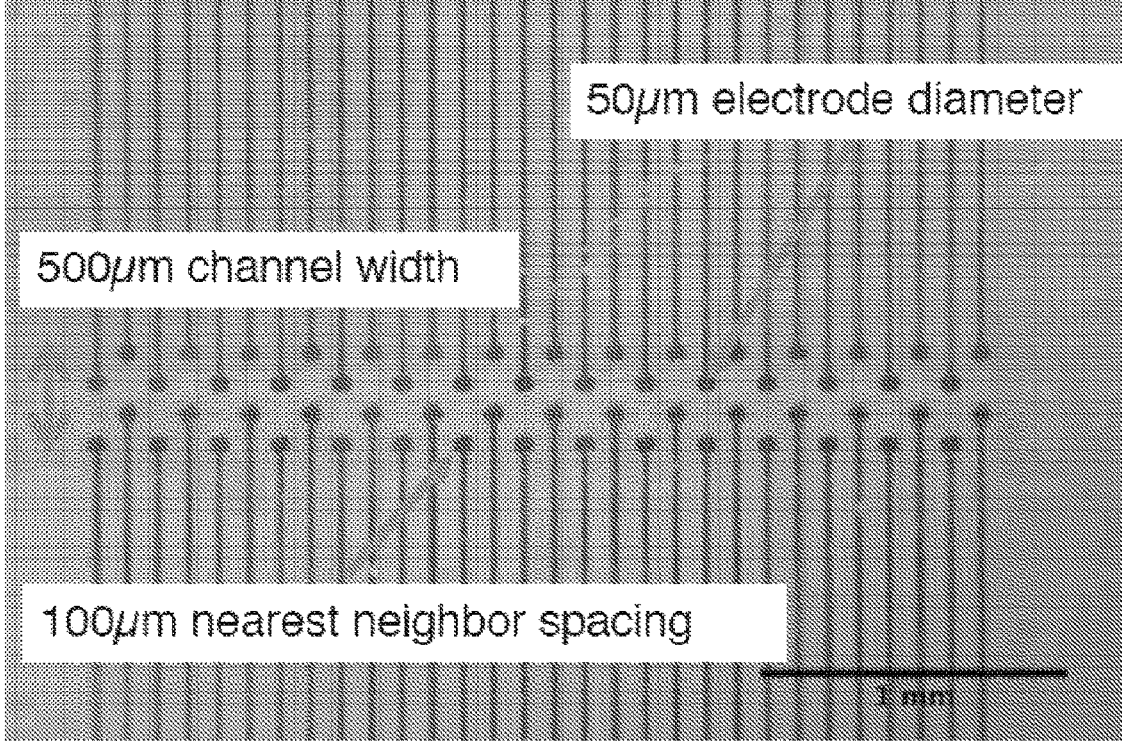
Figure 15:
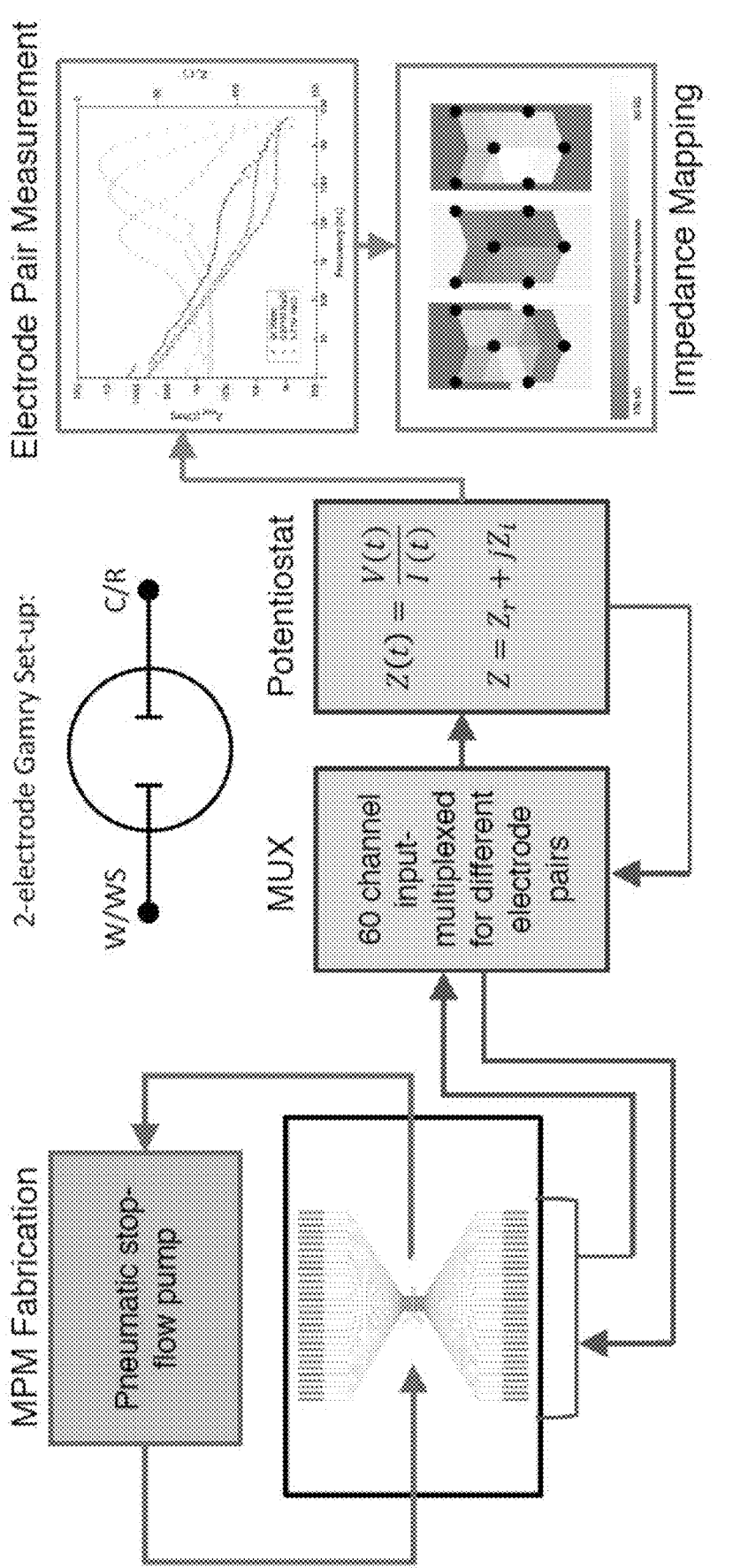
FIG. 15 is an embodiment of a method as described herein showing tissue model creation, electrode pair measurements, and impedance mapping.

The electrode array can be designed as 60 alternating electrodes (30 electrode pairs) that run parallel to the barrier length (FIG. 14A-14B). The electrode array can be fabricated with traditional microfabrication techniques. Electrodes are composed of chromium and gold. Contact lines can be insulated with parylene and 50 μm diameter electrode areas and contact pads are exposed with deep reactive ion etching. Once electrode arrays are fabricated, PDMS channels can be aligned using alignment markers in the top and bottom of the channel. Tissue fabrication can be controlled on top of the electrode array with the previously described pneumatic pump, adjusting flow rates to ensure the engineered tissue is properly oriented along the midline of the electrode array. Each electrode can be connected with a single channel in a multiplexer and 2-point impedance measurements are made between electrode pairs using a Gamry potentiostat. FIG. 15 is an embodiment of a method as described herein showing tissue model creation, electrode pair measurements, and impedance mapping. Frequency can be measured over a 1 Hz to 100 kHz range across pairs of electrodes. Through impedance monitoring partnered with immunohistochemical analysis it can be determined if there is a timelag or overlap between resistance measurements and tight junction degradation, and capacitive measurements and cell viability and transporter function.

Figure 16A:
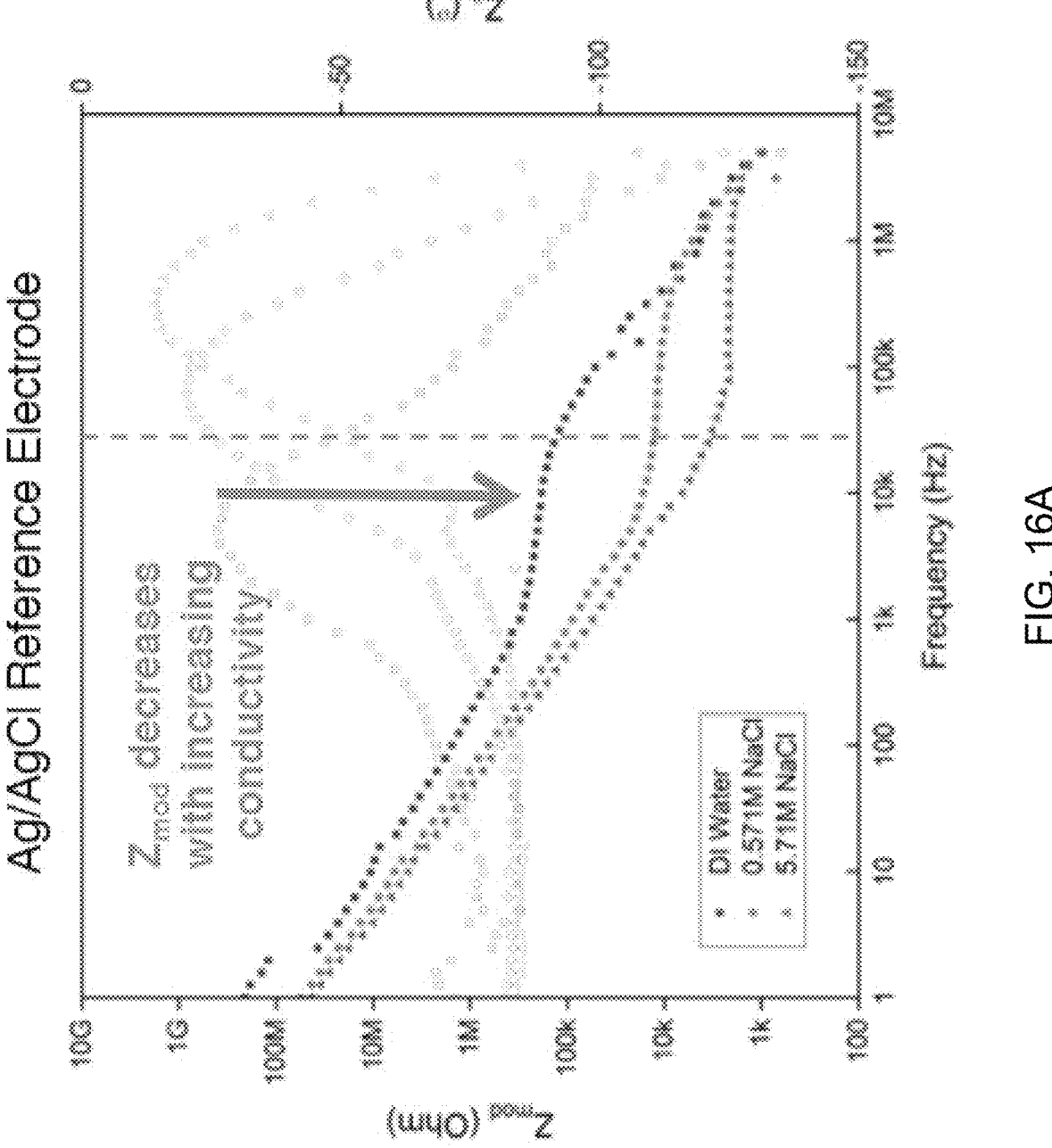
FIGS. 16A-16B show impedance mapping with (FIG. 16A) and without (FIG. 16B) an Ag/AgCl reference electrode. It is noted that tissue models as described herein do not require a reference electrode.
Figure 16B:
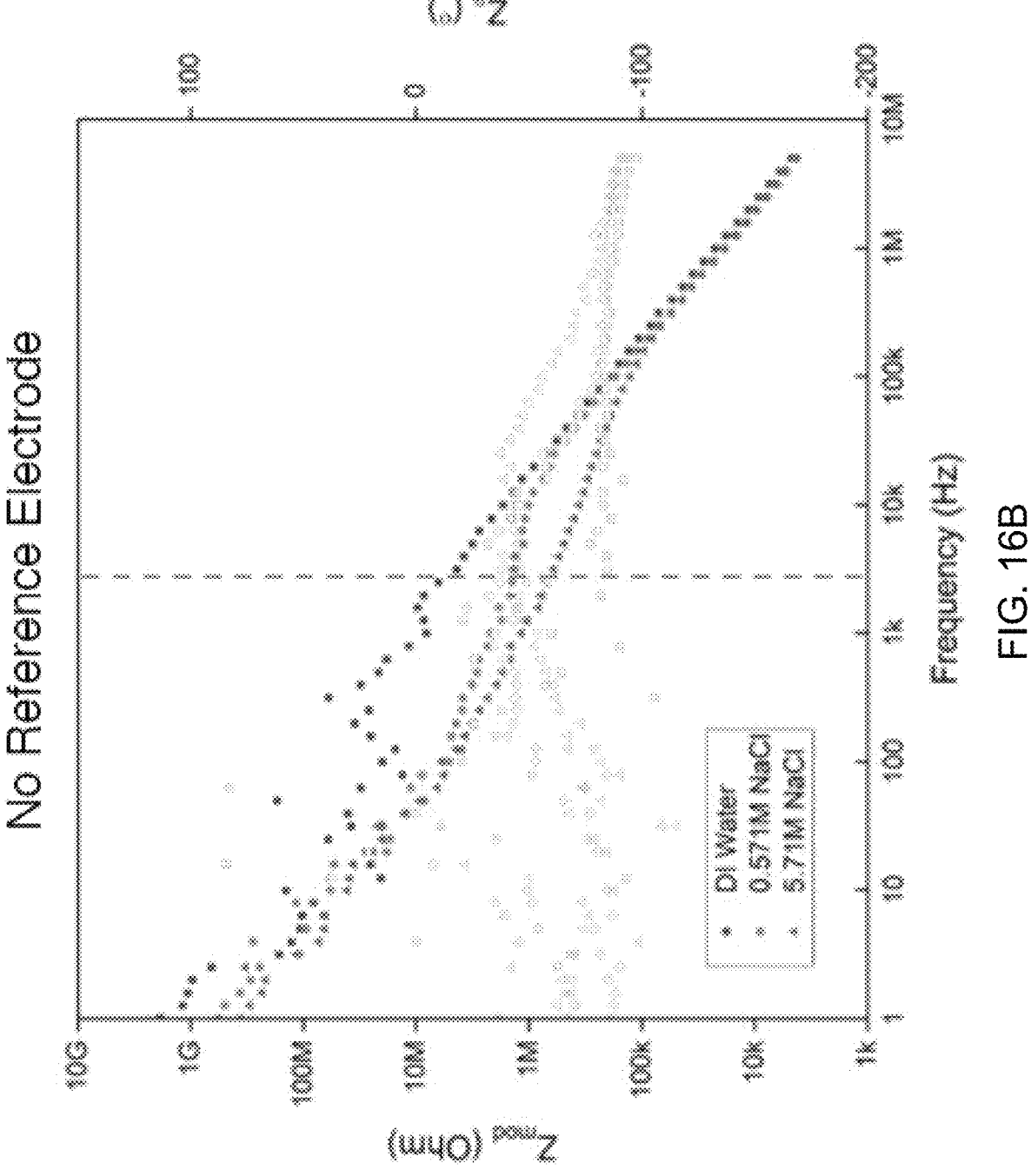
Figure 17A:
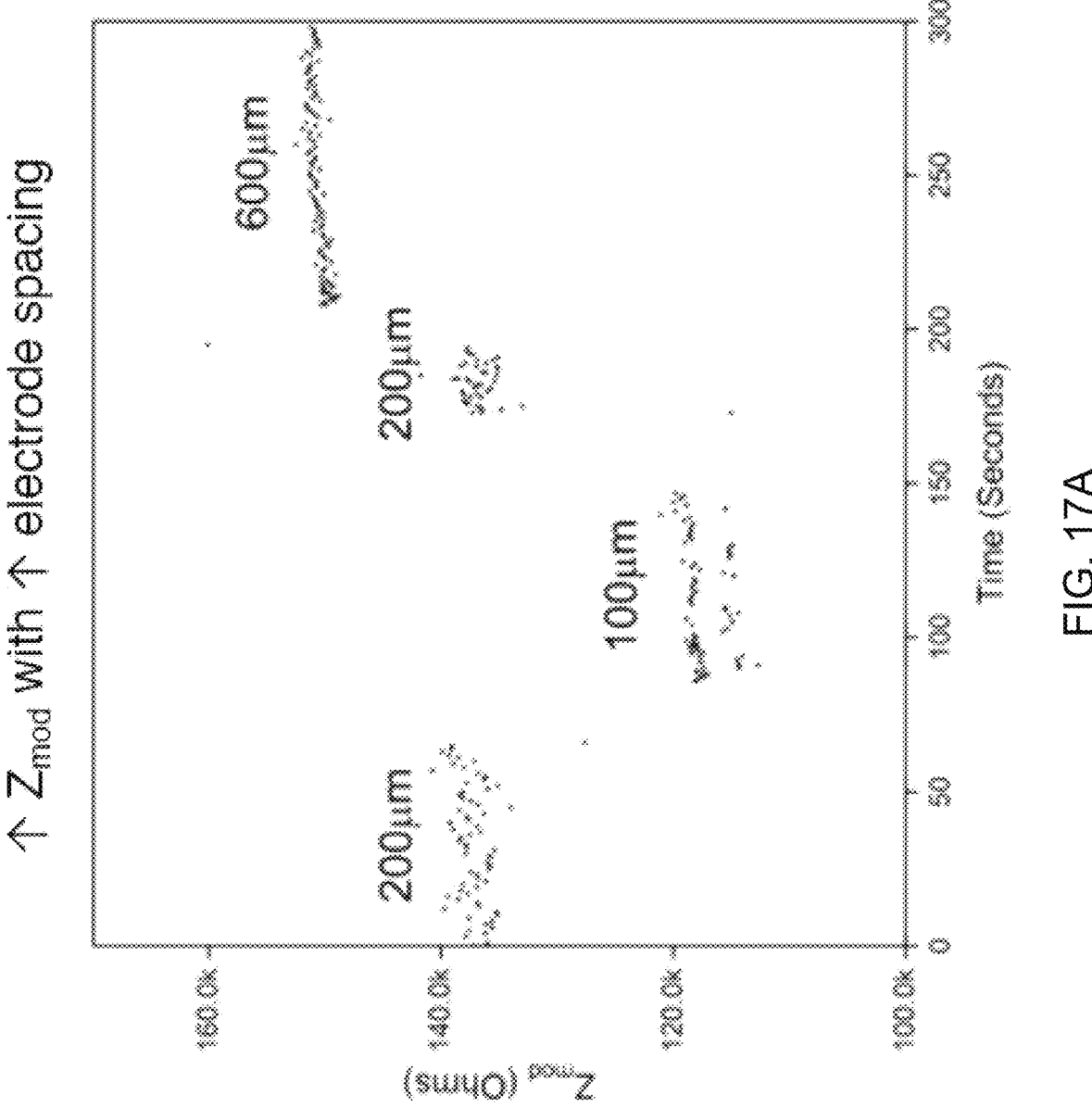
FIGS. 17A-17B are graphs of data of impedance mapping in the flow channel.
Figure 17B:
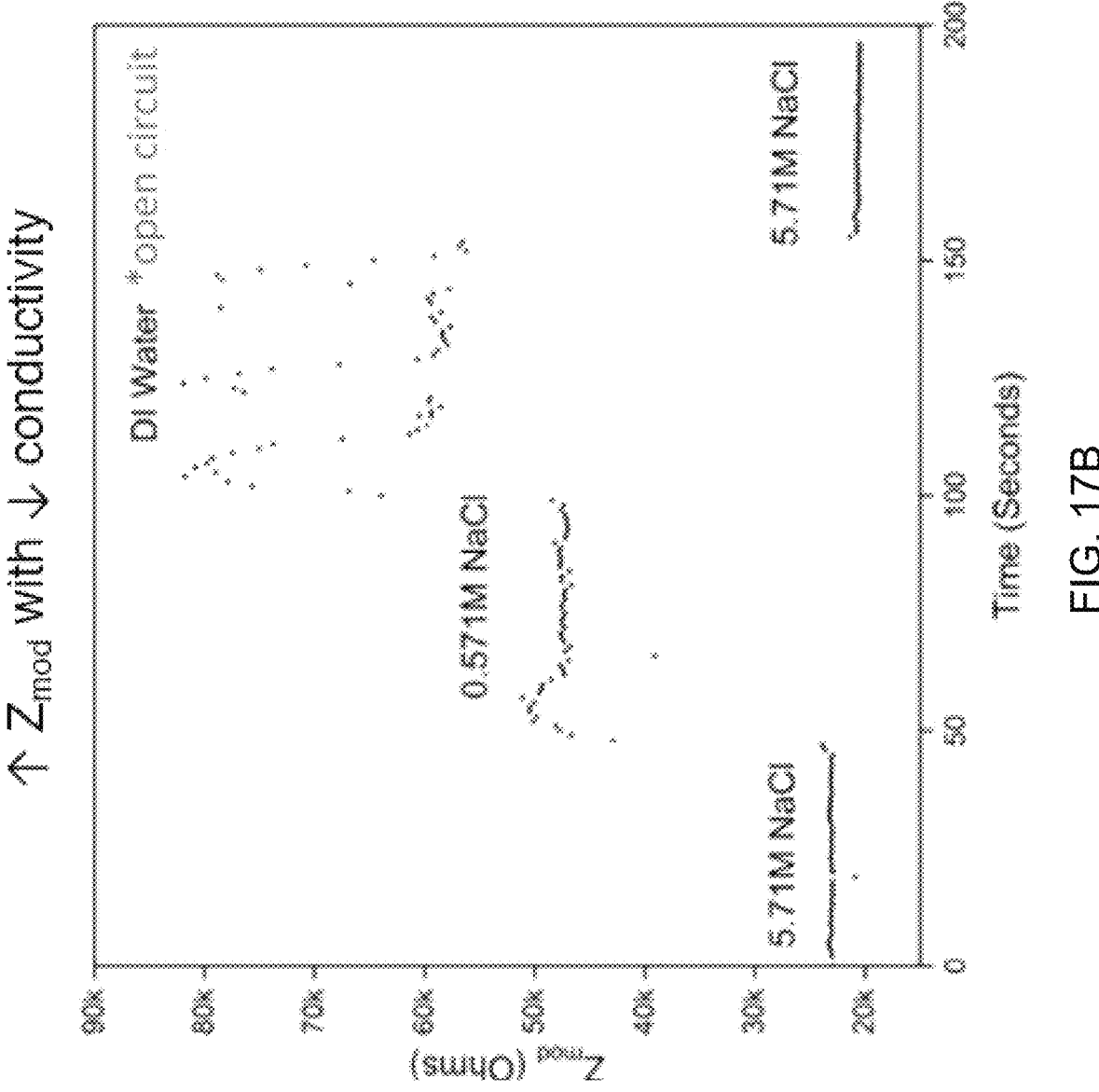
Figure 18:
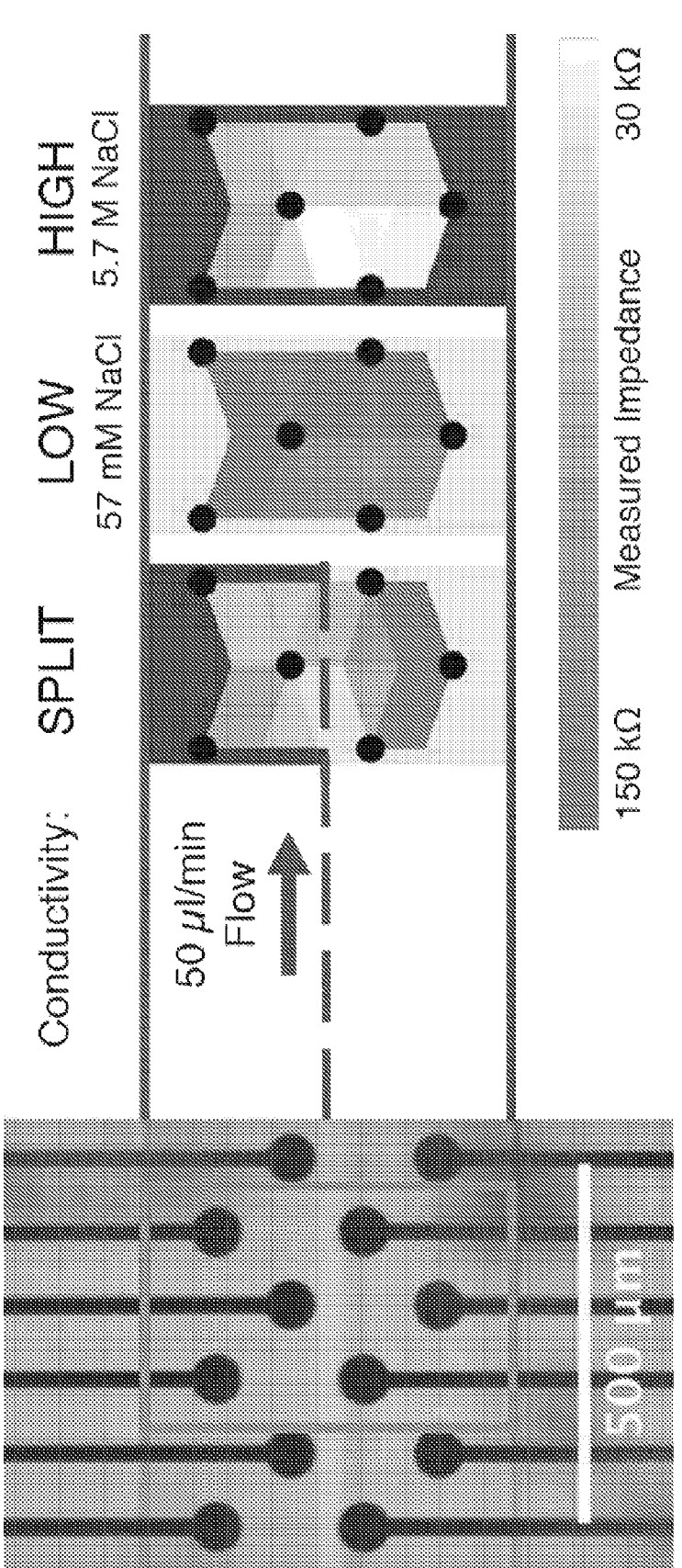
FIG. 18 is another illustration of impedance mapping in the flow channel showing that spatial changes can be detected when sampling from different electrode pairs under flow conditions.
Figure 19:
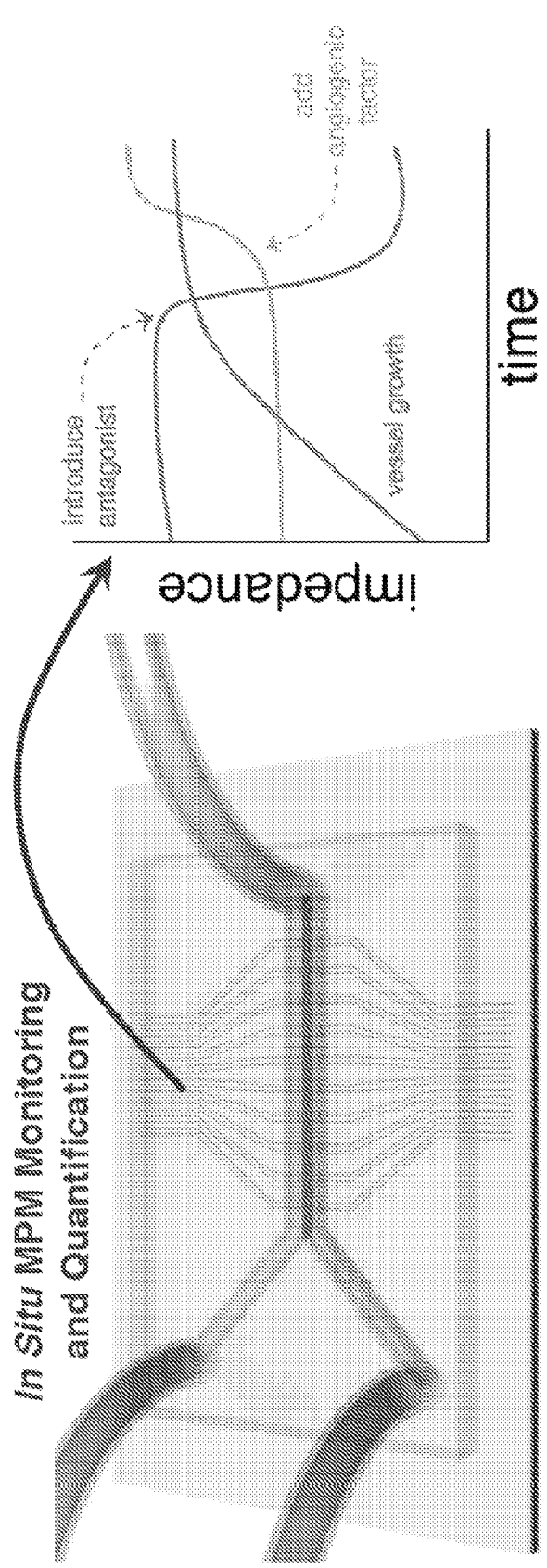
FIG. 19 is an illustration of real-time monitoring of vasculature-tissue barriers (i.e. tissue models).

Data is shown that includes introducing conductive NaCl solutions through the microfluidic channel and collecting two point impedance measurements from 1 Hz to 10 MHz. The measured impedance decreases with increasing conductivity when measured at about 50 kHz with a Ag/AgCl reference electrode, and 5 kHz without a reference electrode (FIGS. 16A-16B). Temporal sensitivity was also demonstrated by showing variable impedance measurements with changing electrode spacing, with the impedance measurement values increasing as the space between electrodes increases (FIGS. 17A-17B). It was also possible to detect a higher impedance with a lower conductivity fluid while pumping different solutions through the microfluidic device. Finally, preliminary 'impedance mapping' capability was demonstrated by flowing high and low conductivity fluids through the microfluidic channel simultaneously, detecting the 'split' laminar flow profile using two point electrode measurements (FIG. 18). By mapping impedance throughout the entire device, the vasculature-tissue interface can be monitored in situ to quantify how tissue models as described herein respond to pharmaceutical compositions (FIG. 19).

Example 3

Microphysiological systems (MPS) incorporate physiologically relevant microanatomy, mechanics, and cells to mimic tissue function. MPS can be used for drug screening, developmental biology, pathology, and toxicology research. Uniquely enabled by in situ formation of 3D tissue, a MPS of the BBB (MPS-BBB) was engineered without a semipermeable membrane, therefore simplifying assembly, enabling high-resolution imaging, and promoting astrocyte-endothelial interactions. Consequently, this system better recapitulates in vivo cellular pathways and functions. Characterization beyond post facto techniques is enabled through impedance monitoring of barrier fidelity with an in-line electrode array. In-line monitoring provides for real-time analyses to infer barrier development, dysfunction, and repair.

The blood-brain barrier (BBB) is the most selective tissue barrier in the body, vital in protecting the brain from pathogens, yet an obstacle to delivering therapeutics for brain disorders. Current BBB-MPSs are limited by semipermeable membranes, single cell types, and 2D culture. This prevents physical contact between cell types and three-dimensional growth within a tissue structure. Current BBB-MPSs are also difficult to assemble, requiring alignment and layering of components. Conventional characterization of MPS function consist of post facto histology or immunohistochemical staining, limiting throughput and translational potential. Transendothelial electrical resistance has been measured on-chip, though with low resolution and high variability. Reproducible and standardized function of MPS is critical for next-generation MPS applications in research and industry. To address current disadvantages, hydrodynamic focusing can be used, in addition to photopolymerizable hydrogel scaffolds and human cell lines to construct tissue-barriers on-chip. Furthermore, electrical impedance measurements can be collected along an in-line electrode array, and processed to create a high-resolution heat map to define tissue growth and barrier selectivity.

Figures 20A, 20B:
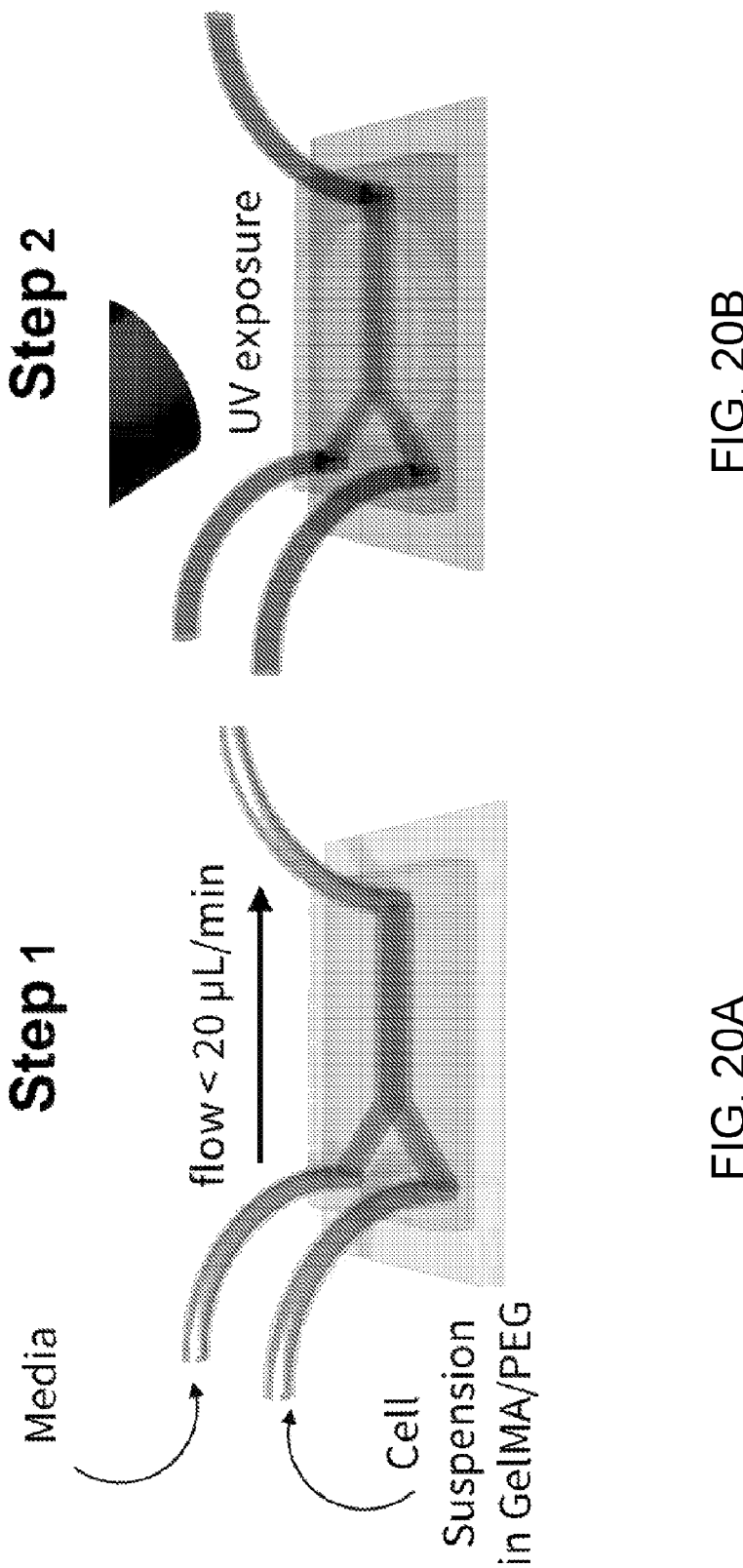

The Y-shaped microfluidic channel is fabricated by soft lithography. Channel dimensions can range from 100 to 500 μm in width and 50 to 150 μm in height. In an embodiment, In situ tissue fabrication is achieved with the introduction of cells in gelatin methacrylamide and PEG-thiol solution, alongside media. Scaffolds can be seeded with human dermal or lung fibroblasts. A laminar flow profile is achieved, stop-flow is initiated, and the scaffold is polymerized by brief exposure to <300 mJ·cm-2 UV light (FIGS. 20A and 20B). Human brain microvascular endothelial cells (hBMVEC) are introduced to the channel and adhere to the tissue structure wall. The BBB-MPM was analyzed post facto by staining for actin, CD-31, and DAPI.

Figure 21A:
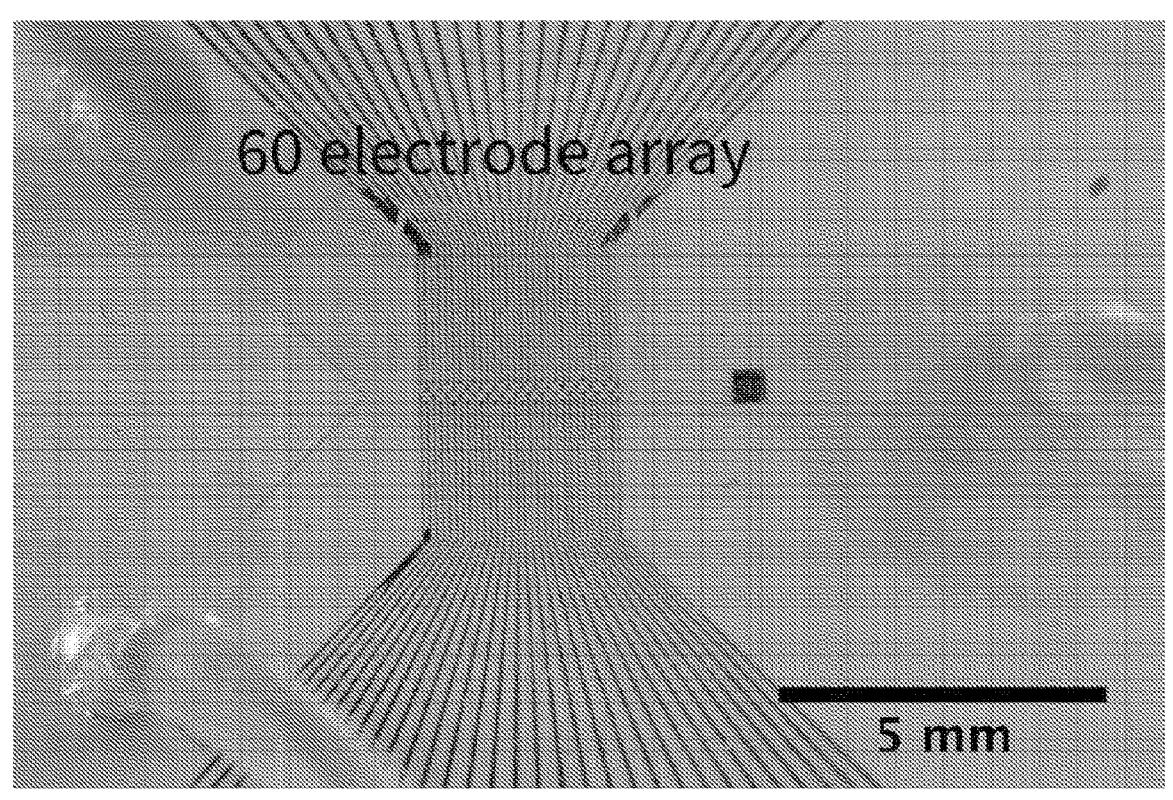
FIGS. 21A-21C.
Figure 21B:
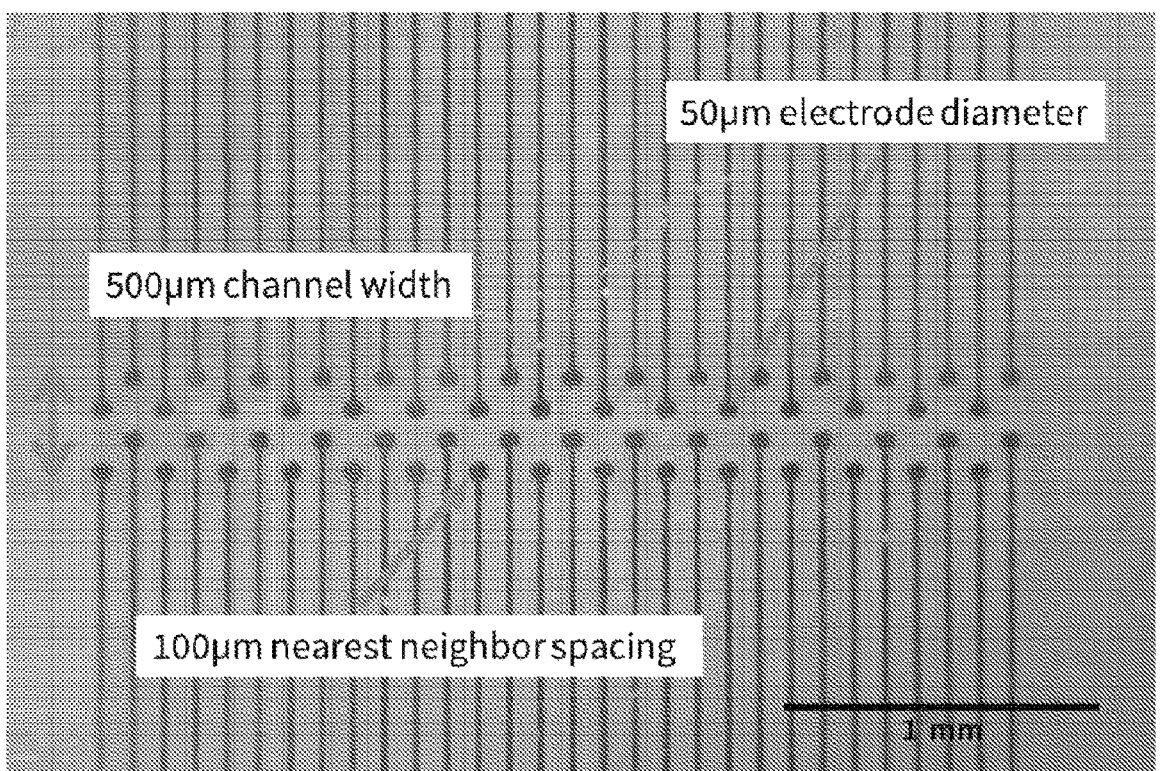

Incorporated electrodes facilitate electrical impedance mapping of the barrier during development and functional assays. A 60-electrode array is fabricated parallel to the barrier length via photolithography and wet etching (FIGS. 21A and 21B). Permutations of 2-wire impedance measurements (1 Hz to 100 kHz) are made along the length of the microchannel using a multiplexer, Gamry potentiostat, and custom Labview code. An impedance "heat map" is created via custom algorithms. Preliminary tests included embedding insulating glass micro-beads in a GeIMA scaffold on-chip with conductive NaCl solutions.

Figure 21C:
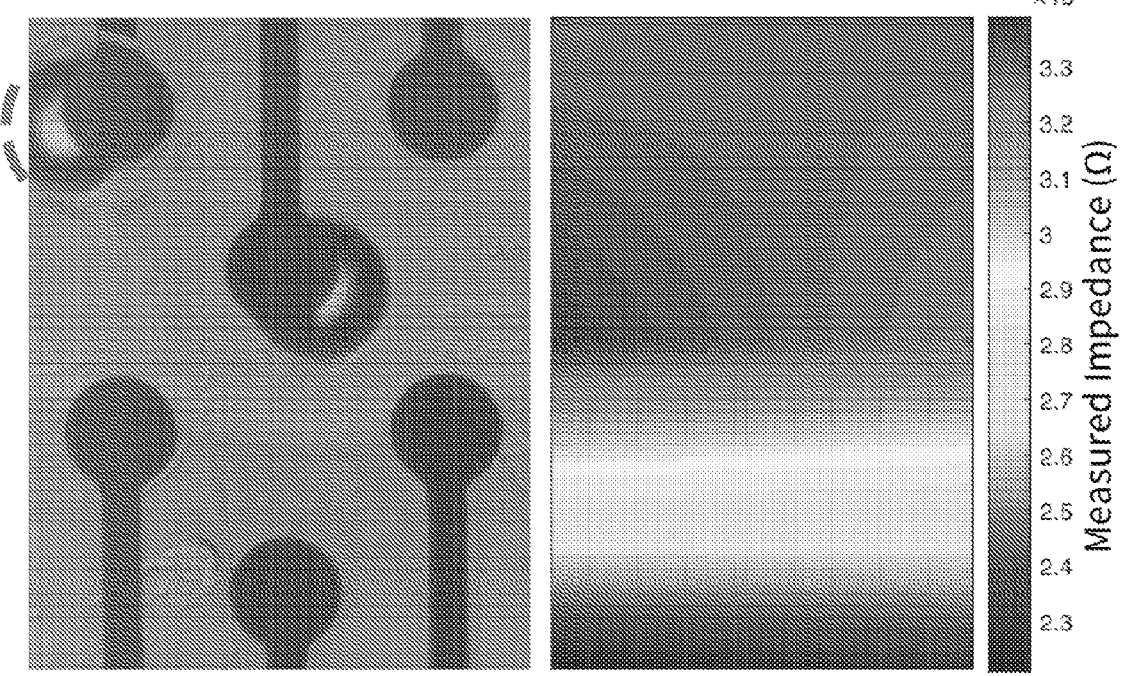

Hydrodynamic focusing, photopolymerizable hydrogel scaffolds, and human cell lines are used to construct tissue-barriers on-chip. A biocompatible hydrogel scaffold is created with healthy cell proliferation, alongside a patent, endothelialized vessel channel. hBMVEC barrier formation and fibroblast adhesion is demonstrated through a 3D scaffold in a microdevice, as well as barrier formation and cell growth down the length of a channel (FIGS. 20C-20E). High resolution imaging of cell proliferation, as well as real-time perfusion studies, are enabled through the vertical orientation of the vessel-tissue interface. Furthermore, vessel development can be tracked, and experimental outcome analyzed in real time with electrical impedance monitoring. Spatial resolution and mapping capabilities are exhibited by using glass microbeads in conductive fluid (FIG. 21C). A novel system and method for high-throughput generation and operation of physiologically-relevant BBB-MPS is demonstrated, enabling discovery of how vasculature interacts with the brain and next generation capabilities for pre-clinical drug testing.

Example 4

FIG. 22 is a flowchart of an embodiment of a method of making a tissue barrier 100 according to the present disclosure. According to the method of making a tissue barrier 100, a microfluidic device is provided 101. A microfluidic device can be a y-junction type device with a first and second input channel that converge into a flow or monitoring channel (see discussion above and drawings) with an output channel. A first solution can be introduced into the first input channel of the microfluidic device 103. A second solution can be introduced into a second input channel of the device 105. The first and second solution can be allowed to flow into the flow channel of the device 107 utilizing passive flow, laminar flow, and/or flow driven by one or more fluid pumps. The flow can then be stopped 109 and a polymerization method applied to the device 111, in particular the flow channel where the first and second solution are mixed. Flow of a third solution in the first input channel, second input channel or both can then be activated 113 and the flow stopped 115 to allow components of the third solution to adhere to aspects of the flow channel.

Example 5

Figure 23:
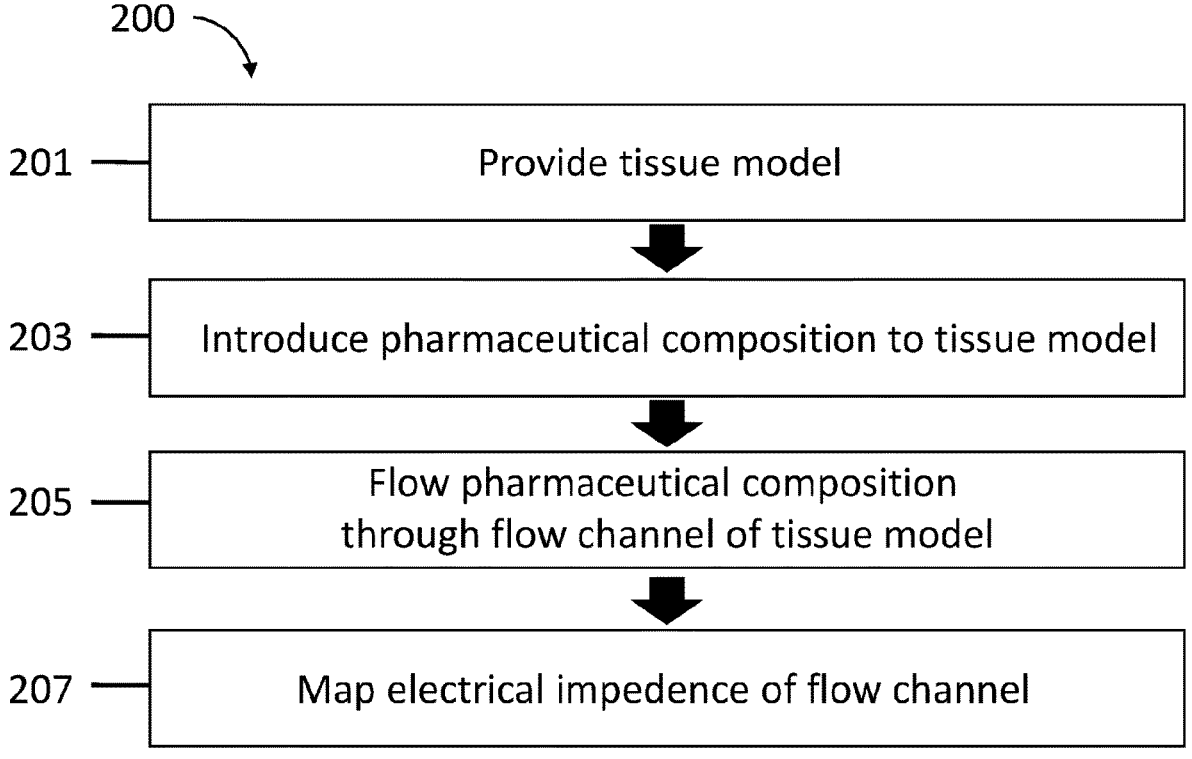
FIG. 23 is a flowchart representative of an embodiment of a method of using a tissue barrier as described herein.

FIG. 23 is a flowchart of an embodiment of using a tissue model according to the present disclosure. According to the method of using 200, a tissue model is provided 201. A pharmaceutical composition is then added to the tissue model 203, which is then allowed to flow into the flow channel 205 (by active or passive flow). Electrical impedance of the flow channel can then be mapped 207, before, after, and/or during flow.

Example 6

Figure 24:
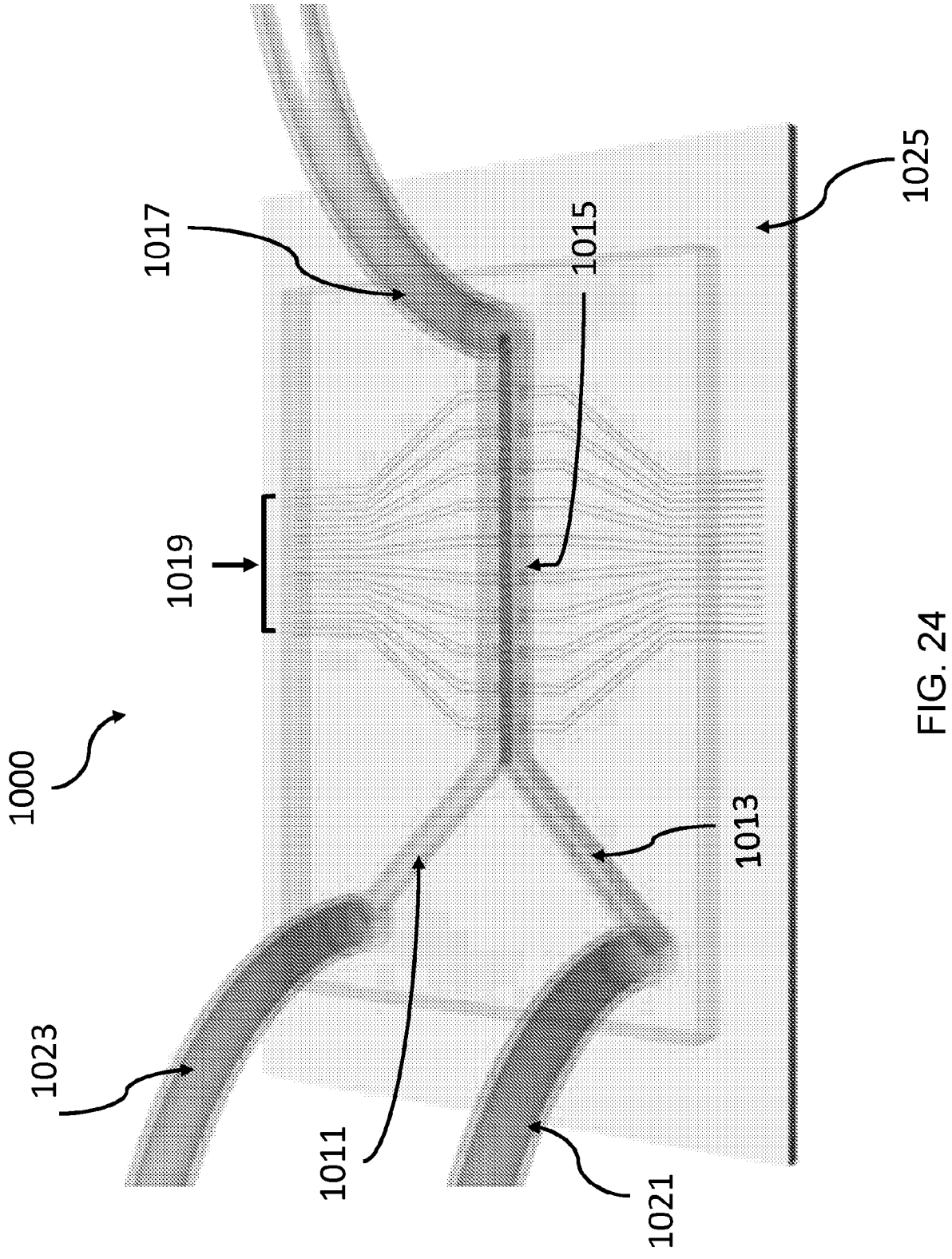
FIG. 24 is an embodiment of a tissue barrier as described herein.

FIG. 24 shows an embodiment of a tissue model 1000 according to the present disclosure. A tissue model 1000 can comprise a first microfluidic input channel 1011 and a second microfluidic input channel 1013. These channels are in fluidic communication with and converge in a microfluidic flow channel 1015 (also referred to herein as a monitoring channel), which is configured to receive flow from the first microfluidic input channel 1011 and second microfluidic input channel 1013. An output channel 1017 is configured to receive flow from the microfluidic flow channel and output solutions from the tissue model. An array of electrodes 1019 can be embedded in the tissue model and configured to monitor (or map) electrical impedance of the flow channel. The first and second microfluidic input channels can further comprise a first conduit 1021 and a second conduit 1023 that are configured to introduce fluids into the first and second microfluidic input channels (1011 and 1013, respectively). The tissue model can further comprise a base 1025 in which the first and second microfluidic input channels (1011 and 1013, respectively) and microfluidic flow channel can be created by a method such as lithography.

Example 7

Figure 25B:
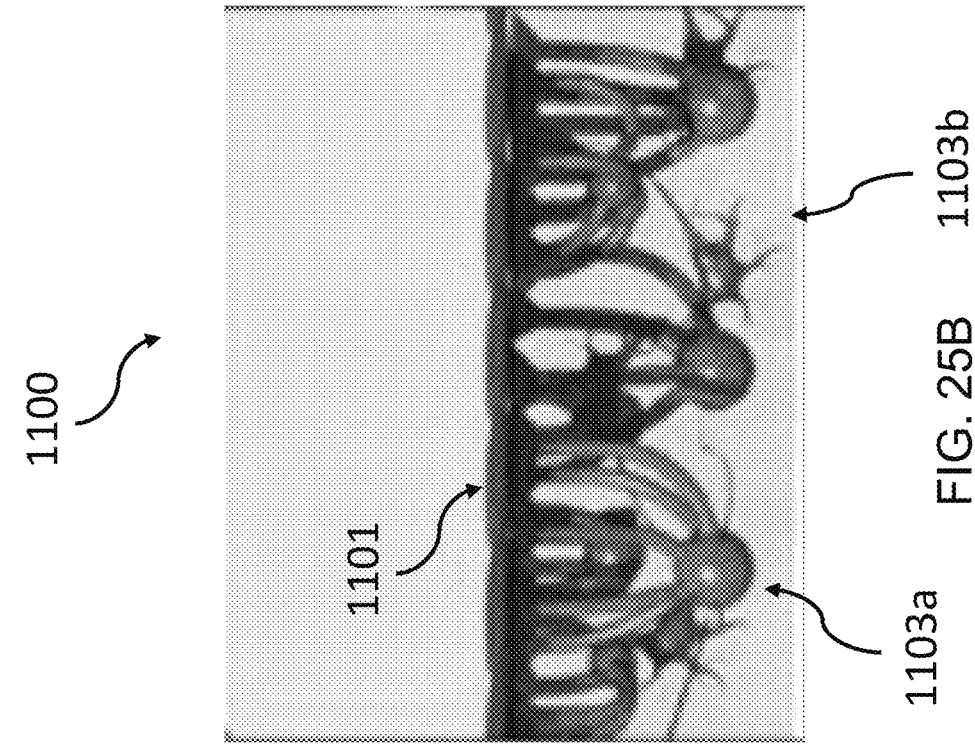
FIGS. 25A and 25B are a cross-sectional view of an embodiment of a microfluidic flow channel of a tissue model as described herein.
Figure 25A:
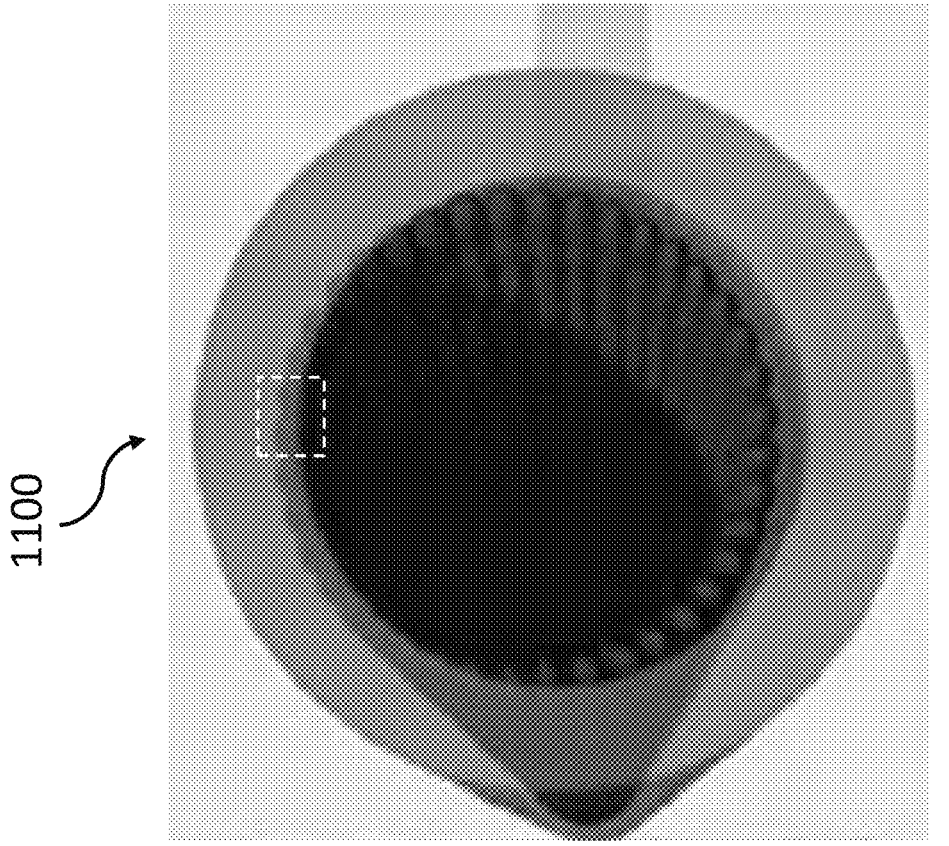

FIG. 25A is an illustration of a cross-sectional view of the microfluidic flow channel 1015 of the tissue model 1000 of FIG. 24. FIG. 25B is an enlarged view. As can be seen from the views, a first cell type 1101 can adhere to the surface 1100 of the microfluidic flow channel (which can comprise a polymeric scaffold as described herein). Additional cell types, such as a second cell type 1103a and a third cell type 1103b can adhere to the first cell type 1101, the inner surface 1100, or both. In the present example, a model of the blood-brain barrier is shown with endothelial cells as the first cell type 1101, astrocytes as the second cell type 1103a, and neurons as the third cell type 1105b.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

Unless defined otherwise, all technical and scientific terms used have the same meaning as commonly understood by one of ordinary skill in the art to which this disclosure belongs. Although any methods and materials similar or equivalent to those described can also be used in the practice or testing of the present disclosure, the preferred methods and materials are now described.

All publications and patents cited in this specification are incorporated by reference as if each individual publication or patent were specifically and individually indicated to be incorporated by reference and are incorporated by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could differ from the actual publication dates that may need to be independently confirmed.

At least the following is claimed:

1. A method of making a tissue model, comprising:
   providing a microfluidic device,
   wherein the microfluidic device comprises two or more input channels on a first end of the device, the two or more input channels converging into a single flow channel in the middle of the device and forming a singular output channel on a second end of the device, and wherein the microfluidic device further comprises a plurality of electrode pairs in electrical connection with the flow channel;
   providing a non-polymerizing first solution into a first channel of the two or more input channels, wherein the non-polymerizing first solution comprises poly-ethylene glycol (PEG), gelatin, or phosphate-buffered saline (PBS);
   providing a polymerizing second solution into a second channel of the two or more input channels, the second solution comprising a photocurable scaffold material;
   allowing the first and the second solution to flow into the flow channel through laminar flow;

stopping flow of the first and second solution;

polymerizing the photocurable scaffold with a polymerization method;

activating flow of a third solution in the first channel, second channel, or both; and stopping the flow of the third solution.

2. The method of claim 1, wherein the non-polymerizing first solution comprises a cell-adherent coating, a scaffold, or both.

3. The method of claim 1, wherein the photocurable scaffold material of the polymerizing second solution comprises a photocurable hydrogel.

4. The method of claim 1, wherein the non-polymerizing first solution, polymerizing second solution, or both further comprise a first plurality of cells.

5. The method of claim 1, wherein the third solution further comprises one or more cell types.

6. The method of claim 1, wherein the polymerization method is applying UV light from a UV light source.

7. The method of claim 4, wherein the third solution comprises a second plurality of cells and a cell media.

8. The method of claim 1, wherein the scaffold of the polymerizing second solution comprises a photocurable polymer and the polymerizing second solution further comprises photoinitiator.

9. The method of claim 3, wherein the photocurable hydrogel is gelatin-methacryloyl (GelMA).

10. The method of claim 1, wherein the tissue model is not fabricated with a synthetic semi-permeable membrane.

11. The method of claim 1, wherein the plurality of electrode pairs comprises greater than 20 electrodes.

12. The method of claim 1, wherein the third solution comprises one or more of a plurality of astrocytes, a plurality of neurons, or a plurality of microglia, individually or in any combination of any thereof.

13. A method of using a tissue model, comprising:

providing a tissue model of claim 1;

providing a solution comprising a pharmaceutical composition into the first channel of the tissue model, second channel, or both;

allowing the solution to flow through the flow channel;

mapping the electrical impedance of the flow channel with the plurality of electrode pairs before, during, or after the flow, individually or in combination.

14. The method of claim 13, wherein the impedance mapping is performed without a reference electrode.

15. A tissue model, comprising:

a first microfluidic input channel;

a second microfluidic input channel;

a microfluidic flow channel comprising a photocured polymeric scaffold on one or more inner surfaces, wherein the photocured polymeric scaffold comprises a UV photocured material and is formed by:

providing a non-polymerizable solution comprising poly-ethylene glycol (PEG), gelatin, or phosphate-buffered saline (PBS) into the first microfluidic input channel and a UV polymerizable solution into the second microfluidic input channel;

providing a flow of the non-polymerizable solution and the UV polymerizable solution from the first microfluidic input channel and second microfluidic input channel into the microfluidic flow channel;

stopping the flow of the non-polymerizable solution and the UV polymerizable solution; and applying UV light to the solutions in the microfluidic flow channel; and a microfluidic output channel in fluidic communication with the microfluidic flow channel, wherein the microfluidic output channel is configured to receive flow from the microfluidic flow channel, wherein the microfluidic flow channel is in fluidic communication with the first microfluidic input channel and second microfluidic input channel, and an end of the microfluidic flow channel is configured to receive flow from the first microfluidic input channel and second microfluidic input channel, and wherein the tissue model is configured so that flow from the first microfluidic input channel and second microfluidic input channel converges at the end of the microfluidic flow channel that receives the flow from the first and second microfluidic flow channels.

16. The tissue model of claim 15, wherein the polymeric scaffold further comprises a first plurality of cells.

17. The tissue model of claim 16, further comprising a second plurality of cells seeded on the first plurality of cells.

18. The tissue model of claim 15, further comprising a plurality of electrode pairs embedded in the flow channel configured to monitor impedance across the length of the channel.

19. The tissue model of claim 15, wherein the polymeric scaffold further comprises a photoinitiator.

20. The tissue model of claim 15, wherein the tissue model does not comprise a synthetic semi-permeable membrane.

* * * * *